(12) United States Patent
Estell et al.

(10) Patent No.: US 6,218,165 B1
(45) Date of Patent: Apr. 17, 2001

(54) MUTANT PROTEINS HAVING LOWER ALLERGENIC RESPONSE IN HUMANS AND METHODS FOR CONSTRUCTING, IDENTIFYING AND PRODUCING SUCH PROTEINS

(75) Inventors: David A. Estell, San Mateo; Fiona A. Harding, Santa Clara, both of CA (US)

(73) Assignee: Genencor International, Inc., Rochester, NY (US)

( * ) Notice: Subject to any disclaimer, the term of this patent is extended or adjusted under 35 U.S.C. 154(b) by 0 days.

(21) Appl. No.: 09/255,502

(22) Filed: Feb. 23, 1999

Related U.S. Application Data

(62) Division of application No. 09/060,872, filed on Apr. 15, 1998.
(51) Int. Cl.[7] ........................................... C12N 9/54
(52) U.S. Cl. ..................... 435/221; 435/263; 435/264; 426/63
(58) Field of Search ............................. 435/221, 263, 435/264; 426/63

(56) References Cited

U.S. PATENT DOCUMENTS 5,801,038 * 9/1998 Bott et al. ............................. 435/221
5,837,517 * 11/1998 Sierkstra et al. ..................... 435/221

FOREIGN PATENT DOCUMENTS

| 0251446 | * | 1/1988 | (EP) . |
| WO 96/34946 | * | 11/1996 | (WO) . |
| WO 98/52976 | | 11/1998 | (WO) . |

* cited by examiner

*Primary Examiner*—David Saunders
(74) *Attorney, Agent, or Firm*—Susan K. Faris; Genencor International, Inc.

(57) ABSTRACT

The present invention relates to a novel improved protein mutant which produces low allergenic response in humans compared to the parent of that mutant. Specifically, the present invention comprises neutralizing or reducing the ability of T-cells to recognize epitopes and thus prevent sensitization of an individual to the protein.

10 Claims, 15 Drawing Sheets

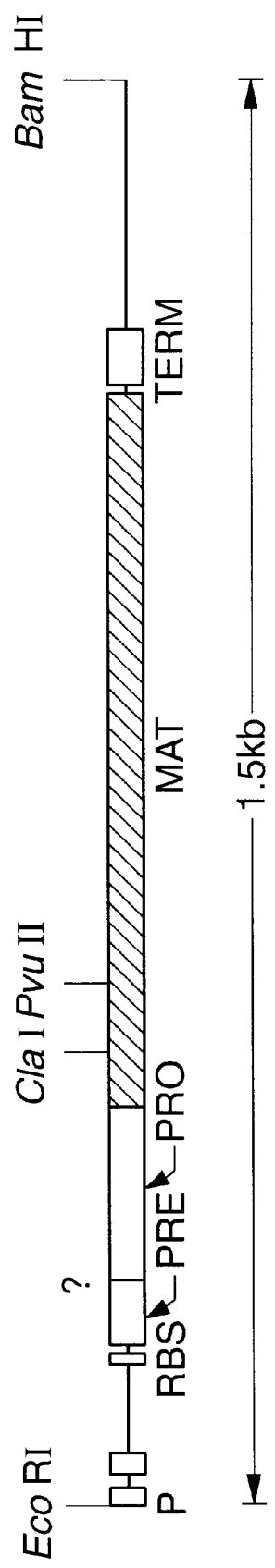
FIG._1A

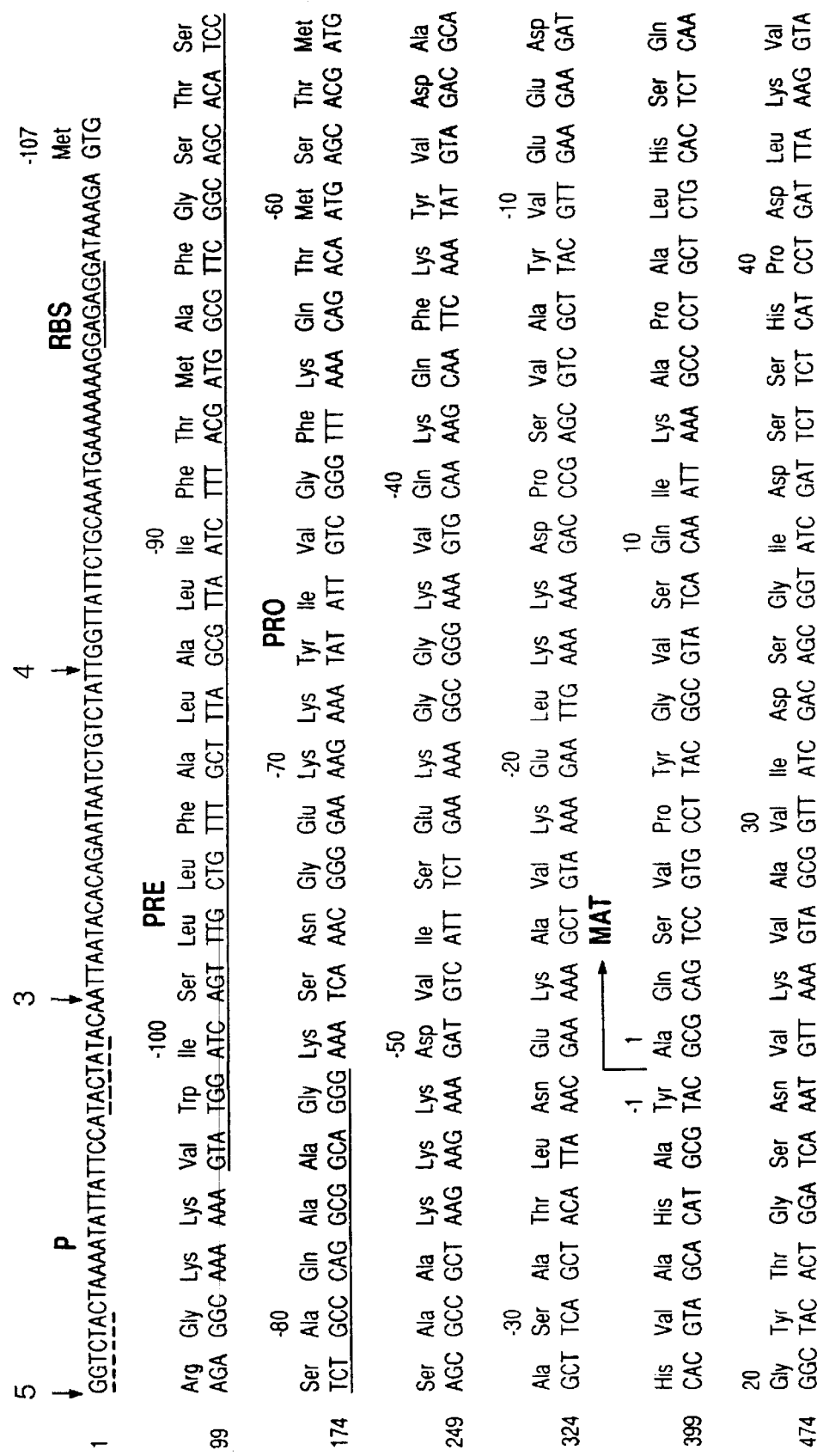
FIG._1B - 1

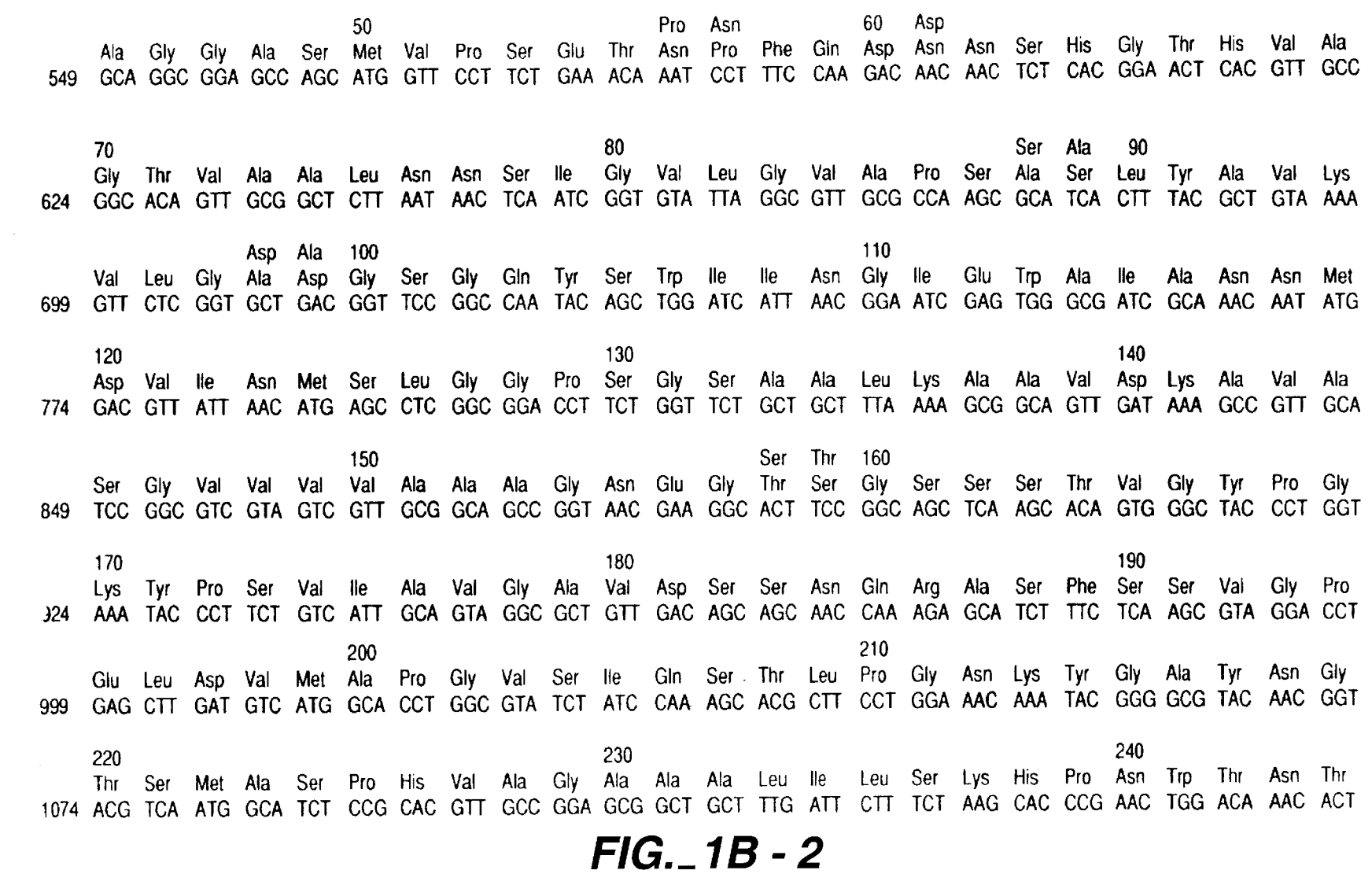

FIG._1B-2

```
       Gln Val Arg Ser Ser Leu Glu Asn Thr Thr Thr Lys Leu Gly Asp Ser Phe Tyr Tyr Gly Lys Gly Leu Ile Asn
                        250                                              260
1149   CAA GTC CGC AGC AGT TTA GAA AAC ACC ACT ACA AAA CTT GGT GAT TCT TTC TAC TAT GGA AAA GGG CTG ATC AAC

Val Gln Ala Ala Ala Gln OC
                 270              275                                                    TERM
1224   GTA CAG GCG GCA GCT CAG TAA  AACATAAAAAAACCGGCCTTGGCCCCGGTTTTTATTTTCTTCCTCCGCATGTTCAATCCGCTCC

1316   ATAATCGACGGATGGCTCCCTCTGAAAATTTTAACGAGAAACGGCGGGTTGACCCGGCTCAGTCCCGTAACGGCCAAGTCCTGAAACGTCTCAATCGCCG

1416   CTTCCCGGGTTTCCGGTCAGCTCAATGCCGTAACGGTCGGGGGCCGTTTCCTGATACCGGGAGACGGCATTCGTAATCGGATC
```

CONSERVED RESIDUES IN SUBTILISINS FROM
*BACILLUS AMYLOLIQUEFACIENS*

COMPARISION OF SUBTILISIN SEQUENCES FROM:
*B.amyloliquefaciens*
*B.subtilis*
*B.licheniformis*
*B.lentus*

```
         170        180        190        200
161 SSTVGYPGKKYPSVIAVGAVDSSNQRASFSSVGPELDVMA
    SSTVGYPAKYPSTIHAVGAVDSSNRASFSSAGSELDVMA
    TSSTIGYPAKYDSVIAVGAVDNSNRASFSSVGAELEVMA
    SS**HSYPARYANAMAVGATDQNNRASFSQYGAGLDIVA 210        220        230        240
201 PGVSIQSTLPGNKYGAYNGTSMASPHVAGAAALILSKHPN
    PGVSIQSTLPGGTYGAYNGTSMATPHVAGAAALILSKHPT
    PGAGVSTYPTNTYATLNGTSMATPHVAGAAALILSKHPN
    PGVNVQSTYPGSTYASLNGTSMATPHVAGAAALVKQKNPS 250        260        270
241 WTNTQVRSSLENTTTKLGDSFYYGKGLINVQAAAAQ
    WTNAQQVRDRLESTATTYLGNSFYYGKGLINVQAAAAQ
    LSASQVRNRLSSTATTYLGSSFYYGKGLINVEAAAAQ
    WSNVQIRNHLKNTATSLGSTNLYGSGLVNAEAATR
```

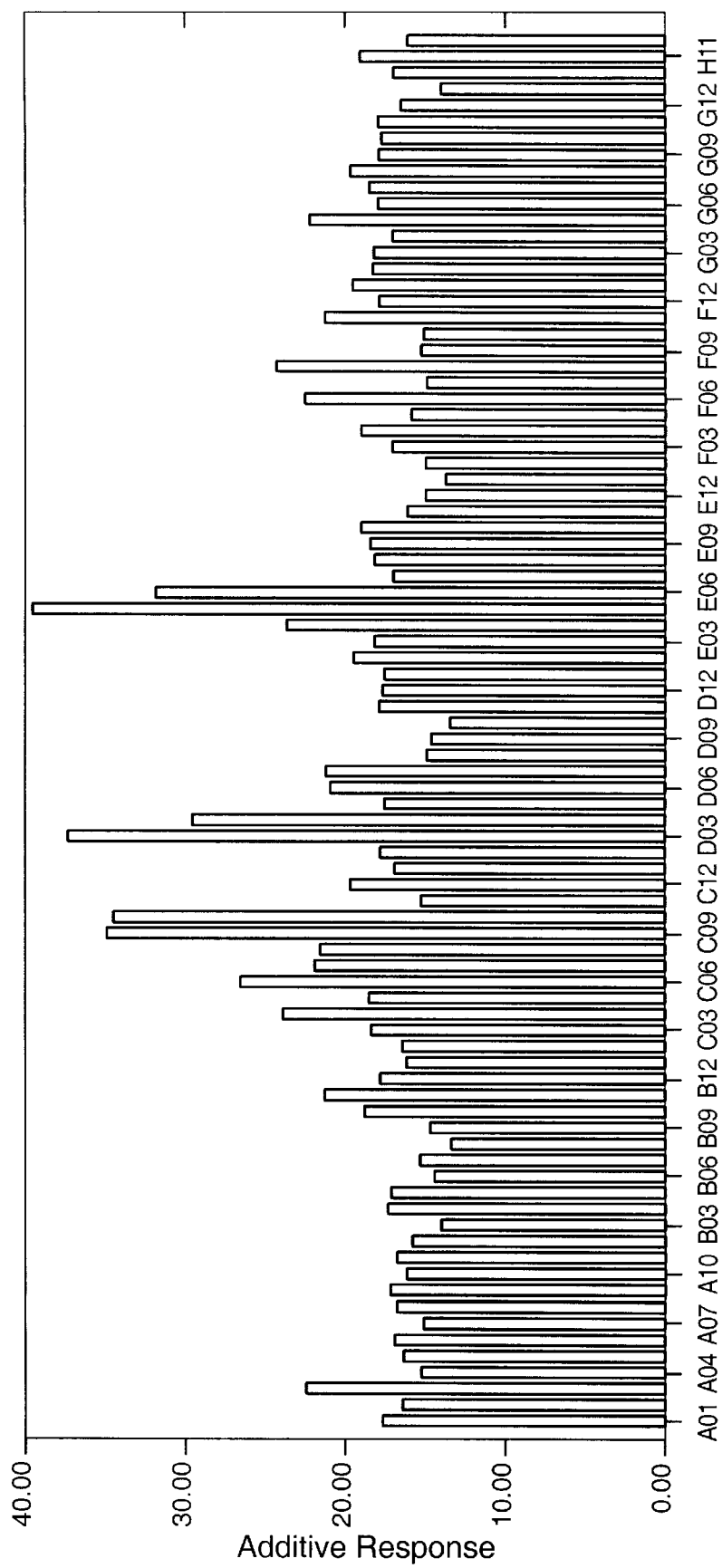
FIG._4

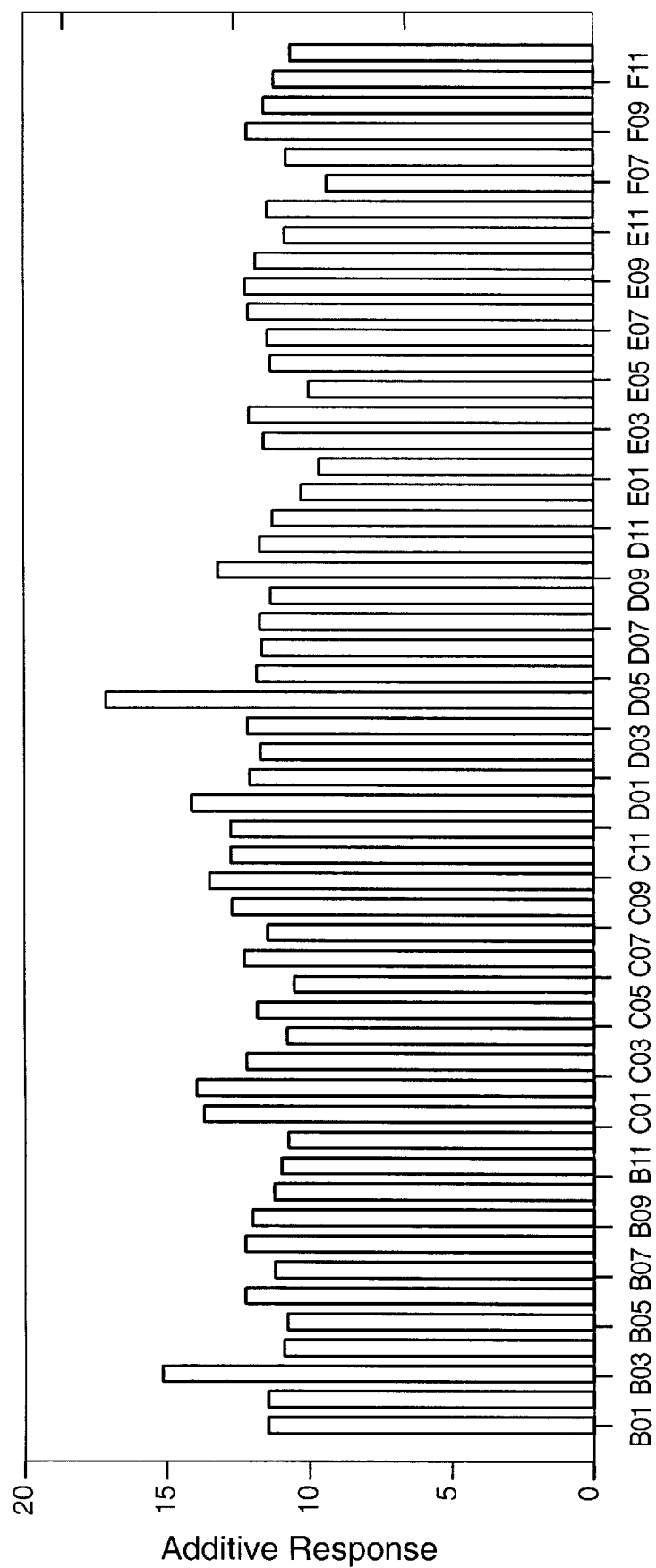
FIG._5

| # | ID | Sequence | # | ID | Sequence |
|---|---|---|---|---|---|
| 1 | A12 | IKDFHVYFRESRDAG | 49 | E12 | SATSRGVLVVAASGN |
| 2 | A11 | LEQAVNSATSRGVLV | 50 | E11 | SRGVLVVAASGNSGA |
| 3 | A10 | AQSVPWGISRVQAPA | 51 | E10 | VLVVAASGNSGAGSI |
| 4 | A9 | VPWGISRVQAPAAHN | 52 | E9 | VAASGNSGAGSISYP |
| 5 | A8 | GISRVQAPAAHNRGL | 53 | E8 | SGNSGAGSISYPARY |
| 6 | A7 | RVQAPAAHNRGLTGS | 54 | E7 | SGAGSISYPARYANA |
| 7 | A6 | APAAHNRGLTGSGVK | 55 | E6 | GSISYPARYANAMAV |
| 8 | A5 | AHNRGLTGSGVKVAV | 56 | E5 | SYPARYANAMAVGAT |
| 9 | A4 | RGLTGSGVKVAVLDT | 57 | E4 | ARYANAMAVGATDQN |
| 10 | A3 | TGSGVKVAVLDTGIS | 58 | E3 | ANAMAVGATDQNNNR |
| 11 | A2 | GVKVAVLDTGISTHP | 59 | E2 | MAVGATDQNNNRASF |
| 12 | A1 | VAVLDTGISTHPDLN | 60 | E1 | GATDQNNNRASFSQY |
| 13 | B12 | LDTGISTHPDLNIRG | 61 | F12 | DQNNNRASFSQYGAG |
| 14 | B11 | GISTHPDLNIRGGAS | 62 | F11 | NNRASFSQYGAGLDI |
| 15 | B10 | THPDLNIRGGASFVP | 63 | F10 | ASFSQYGAGLDIVAP |
| 16 | B9 | DLNIRGGASFVPGEP | 64 | F9 | SQYGAGLDIVAPGVN |
| 17 | B8 | IRGGASFVPGEPSTQ | 65 | F8 | GAGLDIVAPGVNVQS |
| 18 | B7 | GASFVPGEPSTQDGN | 66 | F7 | LDIVAPGVNVQSTYP |
| 19 | B6 | FVPGEPSTQDGNGHG | 67 | F6 | VAPGVNVQSTYPGST |
| 20 | B5 | GEPSTQDGNGHGTHV | 68 | F5 | GVNVQSTYPGSTYAS |
| 21 | B4 | STQDGNGHGTHVAGT | 69 | F4 | VQSTYPGSTYASLNG |
| 22 | B3 | DGNGHGTHVAGTIAA | 70 | F3 | TYPGSTYASLNGTSM |
| 23 | B2 | GHGTHVAGTIAALNN | 71 | F2 | GSTYASLNGTSMATP |
| 24 | B1 | THVAGTIAALNNSIG | 72 | F1 | YASLNGTSMATPHVA |
| 25 | C12 | AGTIAALNNSIGVLG | 73 | G12 | LNGTSMATPHVAGAA |
| 26 | C11 | IAALNNSIGVLGVAP | 74 | G11 | TSMATPHVAGAAALV |
| 27 | C10 | LNNSIGVLGVAPSAE | 75 | G10 | ATPHVAGAAALVKQK |
| 28 | C9 | SIGVLGVAPSAELYA | 76 | G9 | HVAGAAALVKQKNPS |
| 29 | C8 | VLGVAPSAELYAVKV | 77 | G8 | GAAALVKQKNPSWSN |
| 30 | C7 | VAPSAELYAVKVLGA | 78 | G7 | ALVKQKNPSWSNVQI |
| 31 | C6 | SAELYAVKVLGASGS | 79 | G6 | KQKNPSWSNVQIRNH |
| 32 | C5 | LYAVKVLGASGSGSV | 80 | G5 | NPSWSNVQIRNHLKN |
| 33 | C4 | VKVLGASGSGSVSSI | 81 | G4 | WSNVQIRNHLKNTAT |
| 34 | C3 | LGASGSGSVSSIAQG | 82 | G3 | VQIRNHLKNTATSLG |
| 35 | C2 | SGSGSVSSIAQGLEW | 83 | G2 | RNHLKNTATSLGSTN |
| 36 | C1 | GSVSSIAQGLEWAGN | 84 | G1 | LKNTATSLGSTNLYG |
| 37 | D12 | SSIAQGLEWAGNNGM | 85 | H12 | TATSLGSTNLYGSGL |
| 38 | D11 | AQGLEWAGNNGMHVA | 86 | H11 | SLGSTNLYGSGLVNA |
| 39 | D10 | LEWAGNNGMHVANLS | 87 | H10 | STNLYGSGLVNAEAA |
| 40 | D9 | AGNNGMHVANLSLGS | 88 | H9 | NLYGSGLVNAEAATR |
| 41 | D8 | NGMHVANLSLGSPSP | | | |
| 42 | D7 | HVANLSLGSPSPSAT | | | |
| 43 | D6 | NLSLGSPSPSATLEQ | | | |
| 44 | D5 | LGSPSPSATLEQAVN | | | |
| 45 | D4 | PSPSATLEQAVNSAT | | | |
| 46 | D3 | SATLEQAVNSATSRG | | | |
| 47 | D2 | LEQAVNSATSRGVLV | | | |
| 48 | D1 | AVNSATSRGVLVVAA | | | |

*FIG._6A*

| | | | | | | |
|---|---|---|---|---|---|---|
| 1 | A12 | IKDFHVYFRESRDAG | | 49 | E12 | KKIDVLNLSIGGPDF |
| 2 | A11 | DAELHIFRVFTNNQV | | 50 | E11 | DVLNLSIGGPDFMDH |
| 3 | A10 | PLRRASLSLGSGFWH | | 51 | E10 | NLSIGGPDFMDHPFV |
| 4 | A9 | RASLSLGSGFWHATG | | 52 | E9 | IGGPDFMDHPFVDKV |
| 5 | A8 | LSLGSGFWHATGRHS | | 53 | E8 | PDFMDHPFVDKVWEL |
| 6 | A7 | GSGFWHATGRHSSRR | | 54 | E7 | MDHPFVDKVWELTAN |
| 7 | A6 | FWHATGRHSSRRLLR | | 55 | E6 | PFVDKVWELTANNVI |
| 8 | A5 | ATGRHSSRRLLRAIP | | 56 | E5 | DKVWELTANNVIMVS |
| 9 | A4 | RHSSRRLLRAIPRQV | | 57 | E4 | WELTANNVIMVSAIG |
| 10 | A3 | SRRLLRAIPRQVAQT | | 58 | E3 | TANNVIMVSAIGNDG |
| 11 | A2 | LLRAIPRQVAQTLQA | | 59 | E2 | NVIMVSAIGNDGPLY |
| 12 | A1 | AIPRQVAQTLQADVL | | 60 | E1 | MVSAIGNDGPLYGTJ |
| 13 | B12 | RQVAQTLQADVLWQM | | 61 | F12 | AIGNDGPLYGTLNNP |
| 14 | B11 | AQTLQADVLWQMGYT | | 62 | F11 | NDGPLYGTLNNPADQ |
| 15 | B10 | LQADVLWQMGYTGAN | | 63 | F10 | PLYGTLNNPADQMDV |
| 16 | B9 | DVLWQMGYTGANVRV | | 64 | F9 | GTLNNPADQMDVIGV |
| 17 | B8 | WQMGYTGANVRVAVF | | 65 | F8 | NNPADQMDVIGVGGI |
| 18 | B7 | GYTGANVRVAVFDTG | | 66 | F7 | ADQMDVIGVGGIDFE |
| 19 | B6 | GANVRVAVFDTGLSE | | 67 | F6 | MDVIGVGGIDFEDNI |
| 20 | B5 | VRVAVFDTGLSEKHP | | 68 | F5 | IGVGGIDFEDNIARF |
| 21 | B4 | AVFDTGLSEKHPFK | | 69 | F4 | GGIDFEDNIARFSSR |
| 22 | B3 | DTGLSEKHPHFKNVK | | 70 | F3 | DFEDNIARFSSRGMT |
| 23 | B2 | LSEKHPHFKNVKERT | | 71 | F2 | DNIARFSSRGMTTWE |
| 24 | B1 | KHPHFKNVKERTNWT | | 72 | F1 | ARFSSRGMTTWELPG |
| 25 | C12 | HFKNVKERTNWTNER | | 73 | G12 | SSRGMTTWELPGGYG |
| 26 | C11 | NVKERTNWTNERTLD | | 74 | G11 | GMTTWELPGGYGRMK |
| 27 | C10 | ERTNWTNERTLDDGL | | 75 | G10 | TWELPGGYGRMKPDI |
| 28 | C9 | NWTNERTLDDGLGHG | | 76 | G9 | LPGGYGRMKPDIVTY |
| 29 | C8 | NERTLDDGLGHGTFV | | 77 | G8 | GYGRMKPDIVTYGAG |
| 30 | C7 | TLDDGLGHGTFVAGV | | 78 | G7 | RMKPDIVTYGAGVRG |
| 31 | C6 | DGLGHGTFVAGVIAS | | 79 | G6 | PDIVTYGAGVRGSGV |
| 32 | C5 | GHGTFVAGVIASMRE | | 80 | G5 | VTYGAGVRGSGVKGG |
| 33 | C4 | TFVAGVIASMRECQG | | 81 | G4 | GAGVRGSGVKGGCRA |
| 34 | C3 | AGVIASMRECQGFAP | | 82 | G3 | VRGSGVKGGCRALSG |
| 35 | C2 | IASMRECQGFAPDAE | | 83 | G2 | SGVKGGCRALSGTSV |
| 36 | C1 | MRECQGFAPDAELHI | | 84 | G1 | KGGCRALSGTSVASP |
| 37 | D12 | CQGFAPDAELHIFRV | | 85 | H12 | CRALSGTSVASPVVA |
| 38 | D11 | FAPDAELHIFRVFTN | | 86 | H11 | LSGTSVASPVVAGAV |
| 39 | D10 | DAELHIFRVFTNNQV | | 87 | H10 | TSVASPVVAGAVTLL |
| 40 | D9 | LHIFRVFTNNQVSYT | | 88 | H9 | ASPVVAGAVTLLVST |
| 41 | D8 | FRVFTNNQVSYTSWF | | 89 | H8 | VVAGAVTLLVSTVQK |
| 42 | D7 | FTNNQVSYTSWFLDA | | 90 | H7 | GAVTLLVSTVQKREL |
| 43 | D6 | NQVSYTSWFLDAFNY | | 91 | H6 | TLLVSTVQKRELVNP |
| 44 | D5 | SYTSWFLDAFNYAIL | | 92 | H5 | VSTVQKRELVNPASM |
| 45 | D4 | SWFLDAFNYAILKKI | | 93 | H4 | VQKRELVNPASMKQA |
| 46 | D3 | LDAFNYAILKKIDVL | | 94 | H3 | RELVNPASMKQALIA |
| 47 | D2 | FNYAILKKIDVLNLS | | 95 | H2 | VNPASMKQALIASAR |
| 48 | D1 | AILKKIDVLNLSIGG | | 96 | H1 | ASMKQALIASARRLP |

FIG._6B

| | | |
|---|---|---|
| 97 | I12 | IKDFHVYFRESRDAG |
| 98 | I11 | DAELHIFRVFTNNQV |
| 99 | I10 | KQALIASARRLPGVN |
| 100 | I9 | LIASARRLPGVNMFE |
| 101 | I8 | SARRLPGVNMFEQGH |
| 102 | I7 | RLPGVNMFEQGHGKL |
| 103 | I6 | GVNMFEQGHGKLDLL |
| 104 | I5 | MFEQGHGKLDLLRAY |
| 105 | I4 | QGHGKLDLLRAYQIL |
| 106 | I3 | GKLDLLRAYQILNSY |
| 107 | I2 | DLLRAYQILNSYKPQ |
| 108 | I1 | RAYQILNSYKPQASL |
| 109 | J12 | QILNSYKPQASLSPS |
| 110 | J11 | NSYKPQASLSPSYID |
| 111 | J10 | KPQASLSPSYIDLTE |
| 112 | J9 | ASLSPSYIDLTECPY |
| 113 | J8 | SPSYIDLTECPYMWP |
| 114 | J7 | YIDLTECPYMWPYCS |
| 115 | J6 | LTECPYMWPYCSQPI |
| 116 | J5 | CPYMWPYCSQPIYYG |

FIG._6C

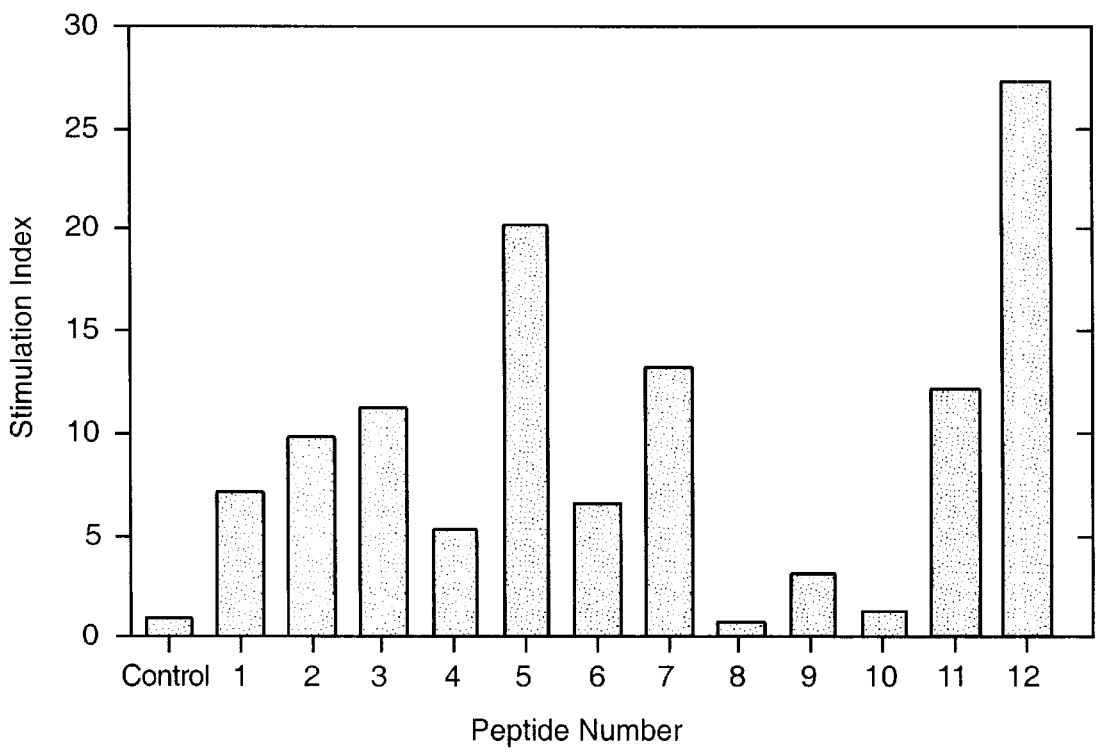

FIG._10

MKLVNIWLLLLVLLCGKKHLGDRLEKKSFEKAPCPGCSHLTLKVEFSSTVVEYEYIVAFNGYFT
AKARNSFISSALKSSEVDNWRIIPRNNPSSDYPSDFEVIQIKEKQKAGLLTLEDHPNIKRVTPQR
KVFRSLKYAESDPTVPCNETRWSQKWQSSRPLRRASLSLGSGFWHATGRHSSRLLRAIPRQVAQ
TLQADVLWQMGYTGANVRVAVFDTGLSEKHPHFKNVKERTNWTNERTLDDGLGHGTFVAGVIASM
RECQGFAPDAELHIFRVFTNNQVSYTSWFLDAFNYAILKIDVLNLSIGGPDFMDHPFVDKVWEL
TANNVIMVSAIGNDGPLYGTLNNPADQMDVIGVGIDFEDNIARFSSRGMTTWELPGGYGRMKPD
IVTYGAGVRGSGVKGGCRALSGTSVASPVVAGAVTLLVSTVQKRELVNPASMKQALIASARRLPG
VNMFEQGHGKLDLLRAYQILNSYKPQASLSPSYIDLTECPYMWPYCSQPIYYGGMPTVVNVTILN
GMGVTGRIVDKPDWQPYLPQNGDNIEVAFSYSSVLWPWSGYLAISISVTKKAASWEGIAQGHVMI
TVASPAETESKNGAEQTSTVKLPIKVKIIPTPPRSKRVLWDQYHNLRYPPGYFPRDNLRMKNDPL
DWNGDHIHTNFRDMYQHLRSMGYFVEVLGAPFTCFDASQYGTLLMVDSEEEYFPEEIAKLRRDVD
NGLSLVIFSDWYNTSVMRKVKFYDENTRQWWMPDTGGANIPALNELLSVWNMGFSDGLYEGEFTL
ANHDMYYASGCSIAKFPEDGVVITQTFKDQGLEVLKQETAVVENVPILGLYQIPAEGGGRIVLYG
DSNCLDDSHRQKDCFWLLDALLQYTSYGVTPPSLSHSGNRQRPPSGAGSVTPERMEGNHLHRYSK
VLEAHLGDPKPRPLPACPRLSWAKPQPLNETAPSNLWKHQKLLSIDLDKVVLPNFRSNRPQVRPL
SPGESGAWDIPGGIMPGRYNQEVGQTIPVFAFLGAMVVLAFFVVQINKAKSRPKRRKPRVKRPQL
MQQVHPPKTPSV

```
                   10          20          30          40          50
BPN'      AQSVPYGVSQ-IKAPALHSQGYTGSNVKVAVIDSGIDSSHPDLK-VAGGA      48
SAVINASE  AQSVPWGISR-VQAPAAHNRGLTGSGVKVAVLDTGI-STHPDLN-IRGGA      47
S2HSBT    -RAIPRQVAQTLQADVLWQMGYTGANVRVAVFDTGLSEKHPHFKNVKERT      49

60          70          80          90         100
BPN'      SMVPSETNPFQDNNSHGTHVAGTVAALNNSIGVLGVAPSASLYAVKVLGA      98
SAVINASE  SFVPGEPST-QDGNGHGTHVAGTIAALNNSIGVLGVAPSAELYAVKVLGA      96
S2HSBT    NW--TNERTLDDGLGHGTFVAGVIASMRECQGF---APDAELHIFRVFTN      94

110         120         130         140         150
BPN'      DGSGQYSWIINGIEWAIANNMDVINMSLGGPS-GSAALKAAVDKAVASGV     147
SAVINASE  SGSGSVSSIAQGLEWAGNNGMHVANLSLGSPS-PSATLEQAVNSATSRGV     145
S2HSBT    NQVSYTSWFLDAFNYAILKKIDVLNLSIGGPDFMDHPFVDKVWELTANNV     144

160         170         180         190         200
BPN'      VVVAAAGNEGTSGSSSTVGYPGKYPSVIAVGAVDSSNQRASFSSVGPEL-     197
SAVINASE  LVVAASGNSGA---GSISYPARYANAMAVGATDQNNNRASFSQYGAGL-     191
S2HSBT    IMVSAIGNDGP--LYGTLNNPADQMDVIGVGGIDFEDNIARFSSRGMTTW     192

210         220         230         240         250
BPN'      -------DVMAPGVSIQSTLPGNKYGAYNGTSMASPHVAGAAALIL         235
SAVINASE  -------DIVAPGVNVQSTYPGSTYASLNGTSMATPHVAGAAALVK         229
S2HSBT    ELPGGYGRMKPDIVTYGAGVRGSGVKGGCRALSGTSVASPVVAGAVTLLV     242

260         270         280         290
BPN'      SKHPNWTNTQ---VRSSLENTTTKLGDSFYYGKGLINVQAAAAQ          275
SAVINASE  QKNPSWSNVQ---IRNHLKNTATSLGSTNLYGSGLVNAEAATR          269
S2HSBT    STVQKRELVNPASMKQALIASARRLPGVNMFEQG---HGKL            280
```

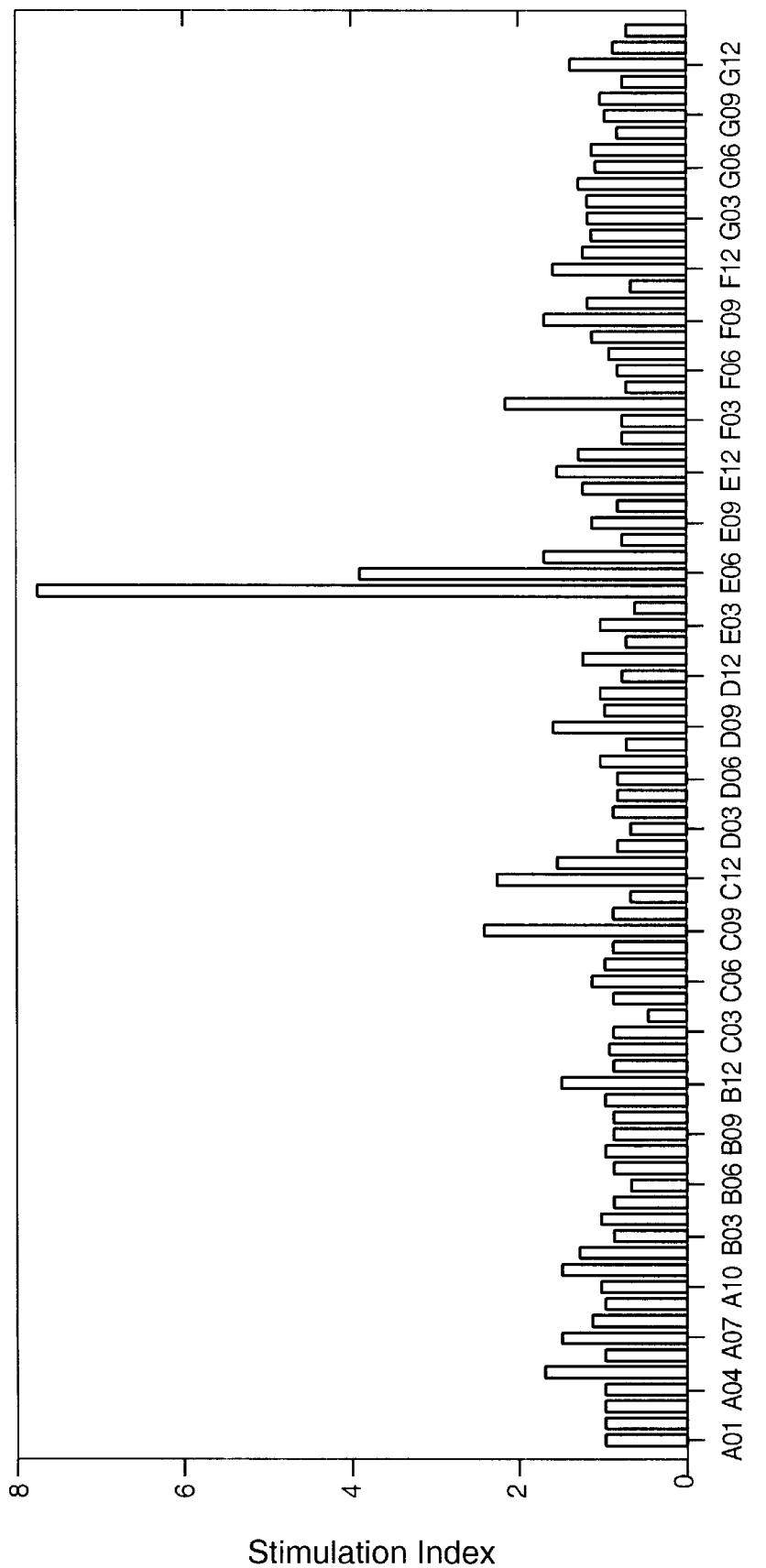
FIG._9

MUTANT PROTEINS HAVING LOWER ALLERGENIC RESPONSE IN HUMANS AND METHODS FOR CONSTRUCTING, IDENTIFYING AND PRODUCING SUCH PROTEINS

CROSS-REFERENCE TO RELATED APPLICATION

This application is a division of application Ser. No. 09/060,872 filed Apr. 15, 1998.

BACKGROUND OF THE INVENTION

A. Field of the Invention

The present invention relates to proteins which produce lower allergenic response in humans exposed to such proteins, and an assay predictive of such response. More specifically, the present invention relates to a novel improved protein mutant which produces very low allergenic response in humans sensitized to that protein through exposure compared to the precursor of such protein mutant.

B. State of the Art

Proteins used in industrial, pharmaceutical and commercial applications are of increasing prevalence. As a result, the increased exposure due to this prevalence has been responsible for some safety hazards caused by the sensitization of certain persons to those peptides, whereupon subsequent exposure causes extreme allergic reactions which can be injurious and even fatal. For example, proteases are known to cause dangerous hypersensitivity in some individuals. As a result, despite the usefulness of proteases in industry, e.g., in laundry detergents, cosmetics, textile treatment etc. . . . , and the extensive research performed in the field to provide improved proteases which have, for example, more effective stain removal under detergency conditions, the use of proteases in industry has been problematic due to their ability to produce a hypersensitive allergic response in some humans.

Much work has been done to alleviate these problems. Among the strategies explored to reduce immunogenic potential of protease use have been improved production processes which reduce potential contact by controlling and minimizing workplace concentrations of dust particles or aerosol carrying airborne protease, improved granulation processes which reduce the amount of dust or aerosol actually produced from the protease product, and improved recovery processes to reduce the level of potentially allergenic contaminants in the final product. However, efforts to reduce the allergenicity of protease, per se, have been relatively unsuccessful. Alternatively, efforts have been made to mask epitopes in protease which are recognized by immunoglobulin E (IgE) in hypersensitive individuals (PCT Publication No. WO 92110755) or to enlarge or change the nature of the antigenic determinants by attaching polymers or peptides/proteins to the problematic protease.

When an adaptive immune response occurs in an exaggerated or inappropriate form, the individual experiencing the reaction is said to be hypersensitive. Hypersensitivity reactions are the result of normally beneficial immune responses acting inappropriately and sometimes cause inflammatory reactions and tissue damage. They can be provoked by many antigens; and the cause of a hypersensitivity reaction will vary from one individual to the next. Hypersensitivity does not normally manifest itself upon first contact with the antigen, but usually appears upon subsequent contact. One form of hypersensitivity occurs when an IgE response is directed against innocuous environmental antigens, such as pollen, dust-mites or animal dander. The resulting release of pharmacological mediators by IgE-sensitized mast cells produces an acute inflammatory reaction with symptoms such as asthma or rhinitis.

Nonetheless, a strategy comprising modifying the IgE sites will not generally be successful in preventing the cause of the initial sensitization reaction. Accordingly, such strategies, while perhaps neutralizing or reducing the severity of the subsequent hypersensitivity reaction, will not reduce the number or persons actually sensitized. For example, when a person is known to be hypersensitive to a certain antigen, the general, and only safe, manner of dealing with such a situation is to isolate the hypersensitive person from the antigen as completely as possible. Indeed, any other course of action would be dangerous to the health of the hypersensitive individual. Thus, while reducing the danger of a specific protein for a hypersensitive individual is important, for industrial purposes it would be far more valuable to render a protein incapable of initiating the hypersensitivity reaction in the first place.

T-lymphocytes (T-cells) are key players in the induction and regulation of immune responses and in the execution of immunological effector functions. Specific immunity against infectious agents and tumors is known to be dependent on these cells and they are believed to contribute to the healing of injuries. On the other hand, failure to control these responses can lead to auto aggression. In general, antigen is presented to T-cells in the form of antigen presenting cells which, through a variety of cell surface mechanisms, capture and display antigen or partial antigen in a manner suitable for antigen recognition by the T-cell. Upon recognition of a specific epitope by the receptors on the surface of the T-cells (T-cell receptors), the T-cells begin a series of complex interactions, including proliferation, which result in the production of antibody by B-cells. While T-cells and B-cells are both activated by antigenic epitopes which exist on a given protein or peptide, the actual epitopes recognized by these mononuclear cells are generally not identical. In fact, the epitope which activates a T-cell to initiate the creation of immunologic diversity is quite often not the same epitope which is later recognized by B-cells in the course of the immunologic response. Thus, with respect to hypersensitivity, while the specific antigenic interaction between the T-cell and the antigen is a critical element in the initiation of the immune response to antigenic exposure, the specifics of that interaction, i.e., the epitope recognized, is often not relevant to subsequent development of a full blown allergic reaction.

PCT Publication No. WO 96140791 discloses a process for producing polyalkylene oxide-polypeptide conjugates with reduced allergenicity using polyalkylene oxide as a starting material.

PCT Publication No. WO 97130148 discloses a polypeptide conjugate with reduced allergenicity which comprises one polymeric carrier molecule having two or more polypeptide molecules coupled covalently thereto.

PCT Publication No. WO 96/17929 discloses a process for producing polypeptides with reduced allergenicity comprising the step of conjugating from 1 to 30 polymolecules to a parent polypeptide.

PCT Publication No. WO 92/10755 discloses a method of producing protein variants evoking a reduced immunogenic response in animals. In this application, the proteins of interest, a series of proteases and variants thereof, were used to immunized rats. The sera from the rats was then used to measure the reactivity of the polyclonal antibodies already produced and present in the immunized sera to the protein of interest and variants thereof. From these results, it was possible to determine whether the antibodies in the preparation were comparatively more or less reactive with the protein and its variants, thus permitting an analysis of which changes in the protein are likely to neutralize or reduce the ability of the Ig to bind. From these tests on rats, the conclusion was arrived at that changing any of subtilisin 309 residues corresponding to 127, 128, 129, 130, 131, 151, 136, 151, 152, 153, 154, 161, 162, 163, 167, 168, 169, 170, 171, 172, 173, 174, 175, 176, 186, 193, 194, 195, 196, 197, 247, 251, 261 will result in a change in the immunological potential.

PCT Publication No. WO 94/10191 discloses low allergenic proteins comprising oligomeric forms of the parent monomeric protein, wherein the oligomer has substantially retained its activity.

The prior art has provided methods of reducing the allergenicity of certain proteins and identification of epitopes which cause allergic reactions in some individuals, the assays used to identify these epitopes generally involving measurement of IgE and IgG antibody in blood sera previously exposed to the antigen. Nonetheless, once an Ig reaction has been initiated, sensitization has already occurred. Accordingly, there is a need for a method of determining epitopes which cause sensitization in the first place, as neutralization of these epitopes will result in significantly less possibility for sensitization to occur, thus reducing the possibility of initial sensitization.

SUMMARY OF THE INVENTION

It is an object of the invention to provide a protein having decreased potential to cause allergenic response in humans compared to a precursor protein.

It is a further object of the present invention to provide for a protease variant which has useful activity in common protease applications, such as detergents and or the treatment of wool to prevent felting, in bar or liquid soap applications, dishcare formulations, contact lens cleaning solutions or products, peptide hydrolysis, waste treatment, textile applications such as anti-felting, in cosmetic formulations and for skin care, or as fusion-cleavage enzymes in protein production, which protease variant can be more safely used due to its lowered allergenic potential.

According to the present invention, a method for identifying T-cell epitopes within a protein is provided. The present invention provides an assay which identifies epitopes as follows: antigen presenting cells are combined with naive human T-cells and with a peptide of interest. In a preferred embodiment of the invention, a method is provided wherein a T-cell epitope is recognized comprising the steps of: (a) obtaining from a single blood source a solution of dendritic cells and a solution of naive CD4+ and/or CD8+ T-cells; (b) promoting differentiation in said solution of dendritic cells; (c) combining said solution of differentiated dendritic cells and said naive CD4+ and/or CD8+ T-cells with a peptide of interest; (d) measuring the proliferation of T-cells in said step (c).

According to another embodiment of the present invention, a protein is provided in which a T-cell epitope is modified so as to reduce or preferably neutralize (eliminate) the ability of the T-cell to identify that epitope. Thus, a protein is provided having reduced allergenicity, wherein said protein comprises a modification comprising the substitution or deletion of amino acid residues which are identified as within a T-cell epitope. According to a preferred embodiment, an epitope is determined in a protein or peptide which, when recognized by a T-cell, results in the proliferation of T-cells which is greater than the baseline. That T-cell epitope is then modified so that, when the peptide comprising the epitope is analyzed in the assay of the invention, it results in lesser proliferation than the protein comprising the unmodified epitope. More preferably, the epitope to be modified produces greater than three times the baseline T-cell proliferation in a sample. When modified, the epitope produces less than three times the baseline T-cell proliferation, preferably less than two times the baseline T-cell proliferation and most preferably less than or substantially equal to the baseline T-ell proliferation in a sample.

Preferably, the epitope is modified in one of the following ways: (a) the amino acid sequence of the epitope is substituted with an analogous sequence from a human homolog to the protein of interest, i.e., human subtilisin or another human protease derived subtilisin like molecule such as furin or the kexins (see e.g., Methods in Enzymology, Vol. 244., (1994) pp 175 et seq; Roebroek et al., EMBO J., Vol. 5, No. 9, pp. 2197–2202 (1986); Tomkinson et al., Biochem., Vol. 30, pp. 168–174 (1991); Keifer et al., DNA and Cell Biol., Vol. 10, No. 10, pp. 757–769 (1991)); (b) the amino acid sequence of the epitope is substituted with an analogous sequence from a non-human homolog to the protein of interest, which analogous sequence produces a lesser allergenic response due to T-cell recognition than that of the protein of interest; (c) the amino acid sequence of the epitope is substituted with a sequence which substantially mimics the major tertiary structure attributes of the epitope, but which produces a lesser allergenic response due to T-cell recognition than that of the protein of interest; or (d) with any sequence which produces lesser allergenic response due to T-cell recognition than that of the protein of interest.

In a specific embodiment of the invention, a protease variant is provided comprising at least one amino acid substitution at a position corresponding to residues 170, 171, 172 and/or 173 in BPN', wherein such substitutions comprise modifying residue 170 to aspartic acid, modifying residue 171 to glutamine, modifying residue 172 to methionine and/or modifying residue 173 to aspartic acid. In a most preferred embodiment, the substitution comprises modifying residues 170, 171 and 173 to aspartic acid, glutamine and aspartic acid, respectively.

In another embodiment of the present invention, a method for producing the protein of the invention having reduced allergenicity is provided. Preferably, the mutant protein is prepared by modifying a DNA encoding a precursor protein so that the modified DNA encodes the mutant protein of the invention.

In yet another embodiment of the invention, DNA sequences encoding the mutant protein, as well as expression vectors containing such DNA sequences and host cells transformed with such vectors are provided, which host cells are preferably capable of expressing such DNA to produce the mutant protein of the invention either intracellularly or extracellulary.

The mutant protein of the invention is useful in any composition or process in which the precursor protein is generally known to be useful. For example, where the protein is a protease, the reduced allergenicity protease can be used as a component in cleaning products such as laundry detergents and hard surface cleansers, as an aid in the preparation of leather, in the treatment of textiles such as wool and/or silk to reduce felting, as a component in a personal care, cosmetic or face cream product, and as a component in animal or pet feed to improve the nutritional value of the feed. Similarly, where the protein is an amylase, the reduce allergenicity amylase can be used for the liquefaction of starch, as a component in a dishwashing detergent, for desizing of textiles, in a laundry detergent or any other use for which amylase is useful.

One advantage of the present invention is that by measuring the proliferation of T-cells due to T-cell epitope recognition, it is possible to identify peptides which contain epitopes responsible for initially sensitizing an individual. That is, T-cell proliferation due to T-cell epitope recognition results in sensitization of an individual to that peptide or a protein which contains it. Neutralization of such "sensitizing" T-cell epitopes will inevitably result in a greater degree of safety for those who handle or are otherwise exposed to the antigen containing the epitope because they will not be initially sensitized, thus preventing the production of Ig antibodies typical of an allergic reaction upon subsequent exposure to the antigen.

An advantage of the present invention is the preparation of proteins, including enzymes, which may be used with significantly less danger of sensitization for the individuals exposed. Thus, for example, the proteins of the invention may be more safely used in cosmetics such as face creams, detergents such as laundry detergents, hard surface cleaning compositions and pre-wash compositions or any other use of protein, including enzymes, wherein human exposure is a necessary by-product.

BRIEF DESCRIPTION OF THE DRAWINGS

FIGS. 1A, B1, B2 and B3 illustrate the DNA (SEQ ID:NO 1) and amino acid (SEQ ID:NO 2) sequence for *Bacillus amyloliquefaciens* subtilisin (BPN') and a partial restriction map of this gene.

FIG. 2 illustrates the conserved amino acid residues among subtilisins from *Bacillus amyloliquefaciens* (SEQ ID:NO 2) and *Bacillus lentus* (wild-type) (SEQ ID:NO 5).

FIGS. 3A and 3B illustrate an amino acid sequence alignment of subtilisin type proteases from *Bacillus amyloliquefaciens* (BPN') (SEQ ID:NO 2), *Bacillus subtilis* (SEQ ID:NO 3), *Bacillus licheniformis* (SEQ ID:NO 4) and *Bacillus lentus* (SEQ ID:NO 5). The symbol * denotes the absence of specific amino acid residues as compared to subtilisin BPN'.

FIG. 4 illustrates the additive T-cell response of 16 peripheral mononuclear blood samples to peptides corresponding to the *Bacillus lentus* protease. Peptide E05 includes the region comprising residues corresponding to 170–173 in protease from *Bacillus amyloliquefaciens*.

FIG. 5 illustrates the additive T-cell response of 10 peripheral mononuclear blood samples to peptides corresponding to the human subtilisin molecule. Peptides F10, F9, F8 and F7 all contain the amino acid sequence DQMD (residues 170–173 of SEQ ID NO; 2) corresponding to the region comprising residues corresponding to 170–173 in protease from *Bacillus amyloliquefaciens* in the sequence alignment of FIG. 3.

FIGS. 6A/6B and FIGS. 6C/6D/6E illustrate amino acid strings corresponding to peptides derived from the sequence of *Bacillus lentus* protease and a human subtilisin, respectively.

FIG. 7 illustrates the amino acid sequence of human subtilisin (SEQ ID:NO 7).

FIG. 8 illustrates an amino acid sequence alignment of BPN' (*Bacillus amyloliquefaciens*) protease (SEQ ID NO: 2), SAVINASE (*Bacillus lentus* (SEQ ID NO: 5)) protease and human subtilisin (S2HSBT (SEQ ID NO: 7)).

FIG. 9 illustrates the T-cell response to peptides derived from *Bacillus lentus* protease in a sample taken from an individual known to be hypersensitive to *Bacillus lentus* protease. Peptide E05 represents the region corresponding to 170–173 in protease from *Bacillus amyloliquefaciens*.

FIG. 10 illustrates the T-cell response to various alanine substitutions in the E05 *Bacillus lentus* protease peptide set in a sample taken from an individual known to be hypersensitive to *Bacillus lentus* protease.

DETAILED DESCRIPTION OF THE INVENTION

According to the present invention, a method for identifying T-cell epitopes is provided. The present invention provides an assay which identifies epitopes as follows: differentiated dendritic cells are combined with naive human CD4+ and/or CD8+ T-cells and with a peptide of interest. More specifically, a method is provided wherein a T-cell epitope is recognized comprising the steps of: (a) obtaining from a single blood source a solution of dendritic cells and a solution of naive CD4+ and/or CD8+ T-cells; (b) promoting differentiation in said solution of dendritic cells; (c) combining said solution of differentiated dendritic cells and said naive CD4+ and/or CD8+ T-cells with a peptide of interest; (d) measuring the proliferation of T-cells in said step (c).

The peptide of interest to be analyzed according to the assay of the invention is derived from a protein or enzyme for which reduced allergenicity is desirable or required. In the practice of the invention, it is possible to identify with precision the location of an epitope which can cause sensitization in an individual or sampling of individuals. In a particularly effective embodiment of the invention, a series of peptide oligomers which correspond to all or part of the protein or enzyme are prepared. For example, a peptide library is produced covering the relevant portion or all of the protein. One particularly useful manner of producing the peptides is to introduce overlap into the peptide library, for example, producing a first peptide corresponds to amino acid sequence 1–10 of the subject protein, a second peptide corresponds to amino acid sequence 4–14 of the subject protein, a third peptide corresponds to amino acid sequence 7–17 of the subject protein, a fourth peptide corresponds to amino acid sequence 10–20 of the subject protein etc. . . . until representative peptides corresponding to the entire molecule are created. By analyzing each of the peptides individually in the assay provided herein, it is possible to precisely identify the location of epitopes recognized by T-cells. In the example above, the reaction of one specific peptide to a greater extent than it's neighbors will facilitate identification of the epitope anchor region to within three amino acids. After determining the location of these epitopes, it is possible to alter the amino acids within each epitope until the peptide produces a less significant T-cell response.

"Antigen presenting cell" as used herein means a cell of the immune system which present antigen on their surface which is recognizable by receptors on the surface of T-cells. Examples of antigen presenting cells are dendritic cells, interdigitating cells, activated B-cells and macrophages.

"T-cell proliferation" as used herein means the number of T-cells produced during the incubation of T-cells with the antigen presenting cells, with or without antigen.

"Baseline T-cell proliferation" as used herein means T-cell proliferation which is normally seen in an individual in response to exposure to antigen presenting cells in the absence of peptide or protein antigen. For the purposes herein, the baseline T-cell proliferation level was determined on a per sample basis for each individual as the proliferation of T-cells in response to antigen presenting cells in the absence of antigen.

"T-cell epitope" means a feature of a peptide or protein which is recognized by a T-cell receptor in the initiation of an immunologic response to the peptide comprising that antigen. Recognition of a T-cell epitope by a T-cell is generally believed to be via a mechanism wherein T-cells recognize peptide fragments of antigens which are bound to class I or class II major histocompatability (MHC) molecules expressed on antigen-presenting cells (see e.g., Moeller, G. ed., Antigenic Requirements for Activation of MHC-Restricted Responses, Immunological Review, Vol. 98, p. 187 (Copenhagen; Munksgaard) (1987).

The epitopes determined according to the assay provided herein are then modified to reduce the allergenic potential of the protein of interest. In a preferred embodiment, the epitope to be modified produces a level of T-cell proliferation of greater than three times the baseline T-cell proliferation in a sample. When modified, the epitope produces less than three times the baseline proliferation, preferably less than two times the baseline proliferation and most preferably less than or substantially equal to the baseline proliferation in a sample.

Preferably, the epitope is modified in one of the following ways: (a) the amino acid sequence of the epitope is substituted with an analogous sequence from a human homolog to the protein of interest; (b) the amino acid sequence of the epitope is substituted with an analogous sequence from a non-human homolog to the protein of interest, which analogous sequence produces a lesser allergenic response due to T-cell epitope recognition than that of the protein of interest; (c) the amino acid sequence of the epitope is substituted with a sequence which substantially mimics the major tertiary structure attributes of the epitope, but which produces a lesser allergenic response due to T-cell epitope recognition than that of the protein of interest; or (d) with any sequence which produces lesser allergenic response due to T-cell epitope recognition than that of the protein of interest.

"Sample" as used herein comprises mononuclear cells which are naive, i.e., not sensitized, to the antigen in question.

"Homolog" as used herein means a protein or enzyme which ha s similar catalytic action, structure and/or use as the protein of interest. It is desirable to find a homolog that has a tertiary and/or primary structure similar to the protein of interest as replacement of the epitope in the protein of interest with an analogous segment from the homolog will reduce the disruptiveness of the change. Thus, closely homologous enzymes will provide the most desirable source of epitope substitutions. Alternatively, if possible, it is advantageous to look to human analogs for a given protein. For example, substituting a specific epitope in a bacterial subtilisin with a sequence from a human analog to subtilisin (i.e., human subtilisin) should result in less allergenicity in the bacterial protein.

An "analogous" sequence may be determined by ensuring that the replacement amino acids show a similar function, the tertiary structure and/or conserved residues to the amino acids in the protein of interest at or near the epitope. Thus, where the epitope region contains, for example, an alpha-helix or a beta-sheet structure, the replacement amino acids should maintain that specific structure.

While the present invention extends to all proteins for which it is desired to reduce allergenicity, for the sake of simplicity, the following will describe a particularly preferred embodiment of the invention, the modification of protease. Proteases are carbonyl hydrolases which generally act to cleave peptide bonds of proteins or peptides. As used herein, "protease" means a naturally-occurring protease or a recombinant protease. Naturally-occurring proteases include α-aminoacylpeptide hydrolase, peptidylamino acid hydrolase, acylamino hydrolase, serine carboxypeptidase, metallocarboxypeptidase, thiol proteinase, carboxylproteinase and metalloproteinase. Seine, metallo, thiol and acid proteases are included, as well as endo and exo-proteases.

Subtilisins are bacterial or fungal proteases which generally act to cleave peptide bonds of proteins or peptides. As used herein, "subtilisin" means a naturally-occurring subtilisin or a recombinant subtilisin. A series of naturally-occurring subtilisins is known to be produced and often secreted by various microbial species. Amino acid sequences of the members of this series are not entirely homologous. However, the subtilisins in this series exhibit the same or similar type of proteolytic activity. This class of serine proteases shares a common amino acid sequence defining a catalytic triad which distinguishes them from the chymotrypsin related class of serine proteases. The subtilisins and chymotrypsin related serine proteases both have a catalytic triad comprising aspartate, histidine and serine. In the subtilisin related proteases the relative order of these amino acids, reading from the amino to carboxy terminus, is aspartate-histidine-serine. In the chymotrypsin related proteases, the relative order, however, is histidine-aspartate-serine. Thus, subtilisin herein refers to a serine protease having the catalytic triad of subtilisin related proteases. Examples include but are not limited to the subtilisins identified in FIG. 3 herein. Generally and for purposes of the present invention, numbering of the amino acids in proteases corresponds to the numbers assigned to the mature *Bacillus amyloliquefaciens* subtilisin sequence presented in FIG. 1.

"Recombinant subtilisin" or "recombinant protease" refer to a subtilisin or protease in which the DNA sequence encoding the subtilisin or protease is modified to produce a variant (or mutant) DNA sequence which encodes the substitution, deletion or insertion of one or more amino acids in the naturally-occurring amino acid sequence. Suitable methods to produce such modification, and which may be combined with those disclosed herein, include those disclosed in U.S. Pat. No. 4,760,025 (RE 34,606), U.S. Pat. No. 5,204,015 and U.S. Pat. No. 5,185,258.

"Non-human subtilisins" and the DNA encoding them may be obtained from many procaryotic and eucaryotic organisms. Suitable examples of procaryotic organisms include gram negative organisms such as *E. coli* or Pseudomonas and gram positive bacteria such as Micrococcus or Bacillus. Examples of eucaryotic organisms from which subtilisin and their genes may be obtained include yeast such as *Saccharomyces cerevisiae,* fungi such as *Aspergillus sp.*

"Human subtilisin" means proteins of human origin which have subtilisin type catalytic activity, e.g., the kexin family of human derived proteases. An example of such a protein is represented by the sequence in FIG. 7. Additionally, derivatives or homologs of human subtilisin, including those from non-human sources such as mouse or rabbit, which retain the essential ability to hydrolyze peptide bonds and have at least 50%, preferably at least 65% and most preferably at least 80% homology to the protein of FIG. 7 are considered human subtilisins for the purpose of the invention.

A "protease variant" has an amino add sequence which is derived from the amino acid sequence of a "precursor protease". The precursor proteases include naturally-occurring proteases and recombinant proteases. The amino acid sequence of the protease variant is "derived" from the precursor protease amino acid sequence by the substitution, deletion or insertion of one or more amino acids of the precursor amino acid sequence. Such modification is of the "precursor DNA sequence" which encodes the amino acid sequence of the precursor protease rather than manipulation of the precursor protease enzyme per se. Suitable methods for such manipulation of the precursor DNA sequence include methods disclosed herein, as well as methods known to those skilled in the art (see, for example, EP 0 328299, W089/06279 and the US patents and applications already referenced herein).

The amino acid position numbers used herein refer to those assigned to the mature *Bacillus amyloliquefaciens* subtilisin sequence presented in FIG. 1. The invention, however, is not limited to the mutation of this particular subtilisin but extends to precursor proteases containing amino acid residues at positions which are "equivalent" to the particular identified residues in *Bacillus amyloliquefaciens* subtilisin. In a preferred embodiment of the present invention, the precursor protease is *Bacillus lentus* subtilisin and the substitutions, deletions or insertions are made at the equivalent amino acid residue in *B. lentus* corresponding to those listed above.

A residue (amino acid) of a precursor protease is equivalent to a residue of *Bacillus amyloliquefaciens* subtilisin if it is either homologous (i.e., corresponding in position in either primary or tertiary structure) or analogous to a specific residue or portion of that residue in *Bacillus amyloliquefaciens* subtilisin (i.e., having the same or similar functional capacity to combine, react, or interact chemically).

In order to establish homology to primary structure, the amino acid sequence of a precursor protease is directly compared to the *Bacillus amyloliquefaciens* subtilisin primary sequence and particularly to a set of residues known to be invariant in subtilisins for which the sequence is known. For example, FIG. 2 herein shows the conserved residues as between *B. amyloliquefaciens* subtilisin and *B. lentus* subtilisin. After aligning the conserved residues, allowing for necessary insertions and deletions in order to maintain alignment (i.e., avoiding the elimination of conserved residues through arbitrary deletion and insertion), the residues equivalent to particular amino acids in the primary sequence of *Bacillus amyloliquefaciens* subtilisin are defined. Alignment of conserved residues preferably should conserve 100% of such residues. However, alignment of greater than 75% or as little as 50% of conserved residues is also adequate to define equivalent residues. Conservation of the catalytic triad, Asp32/His64/Ser221 should be maintained.

For example, the amino acid sequence of subtilisin from *Bacillus amyloliquefaciens, Bacillus subtilis, Bacillus licheniformis* (carlsbergensis) and *Bacillus lentus* can be aligned to provide the maximum amount of homology between amino acid sequences. A comparison of these sequences shows that there are a number of conserved residues contained in each sequence. The conserved residues as between BPN' and *B. lentus* are identified in FIG. 2.

These conserved residues, thus, may be used to define the corresponding equivalent amino acid residues of *Bacillus amyloliquefaciens* subtilisin in other subtilisins such as subtilisin from *Bacillus lentus* (PCT Publication No. W089106279 published Jul. 13, 1989), the preferred protease precursor enzyme herein, or the subtilisin referred to as PB92 (EP 0 328 299), which is highly homologous to the preferred *Bacillus lentus* subtilisin. The amino acid sequences of certain of these subtilisins are aligned in FIGS. 3A and 3B with the sequence of *Bacillus amyloliquefaciens* subtilisin to produce the maximum homology of conserved residues. As can be seen, there are a number of deletions in the sequence of *Bacillus lentus* as compared to *Bacillus amyloliquefaciens* subtilisin. Thus, for example, the equivalent amino acid for Val165 in *Bacillus amyloliquefaciens* subtilisin in the other subtilisins is isoleucine for *B. lentus* and *B. licheniformis*.

Thus, for example, the amino acid at position +170 is lysine (K) in both *B. amyloliquefaciens* and *B. licheniformis* subtilisins and arginine (R) in Savinase. In one embodiment of the protease variants of the invention, however, the amino acid equivalent to +170 in *Bacillus amyloliquefaciens* subtilisin is substituted with aspartic acid (D). The abbreviations and one letter codes for all amino acids in the present invention conform to the Patent In User Manual (GenBank, Mountain View, Calif.) 1990, p.101.

"Equivalent residues" may also be defined by determining homology at the level of tertiary structure for a precursor protease whose tertiary structure has been determined by x-ray crystallography. Equivalent residues are defined as those for which the atomic coordinates of two or more of the main chain atoms of a particular amino acid residue of the precursor protease and *Bacillus amyloliquefaciens* subtilisin (N on N, CA on CA, C on C and O on O) are within 0.13nm and preferably 0.1 nm after alignment. Alignment is achieved after the best model has been oriented and positioned to give the maximum overlap of atomic coordinates of non-hydrogen protein atoms of the protease in question to the *Bacillus amyloliquefaciens* subtilisin. The best model is the crystallographic model giving the lowest R factor for experimental diffraction data at the highest resolution available.

$$R \text{ factor} = \frac{\sum_h |Fo(h)| - |Fc(h)|}{\sum_h |Fo(h)|}$$

Equivalent residues which are functionally analogous to a specific residue of *Bacillus amyloliquefaciens* subtilisin are defined as those amino acids of the precursor protease which may adopt a conformation such that they either alter, modify or contribute to protein structure, substrate binding or catalysis in a manner defined and attributed to a specific residue of the *Bacillus amyloliquefaciens* subtilisin. Further, they are those residues of the precursor protease (for which a tertiary structure has been obtained by x-ray crystallography) which occupy an analogous position to the extent that, although the main chain atoms of the given residue may not satisfy the criteria of equivalence on the basis of occupying a homologous position, the atomic coordinates of at least two of the side chain atoms of the residue lie with 0.13 nm of the corresponding side chain atoms of *Bacillus amyloliquefaciens* subtilisin. The coordinates of the three dimensional structure of *Bacillus amyloliquefaciens* subtilisin are set forth in EPO Publication No. 0 251 446 (equivalent to U.S. Pat. No. 5,182,204, the disclosure of which is incorporated herein by reference) and can be used as outlined above to determine equivalent residues on the level of tertiary structure.

Some of the residues identified for substitution, insertion or deletion are conserved residues whereas others are not. In the case of residues which are not conserved, the replacement of one or more amino acids is limited to substitutions which produce a variant which has an amino acid sequence that does not correspond to one found in nature. In the case of conserved residues, such replacements should not result in a naturally-occurring sequence. The protease variants of the present invention include the mature forms of protease variants, as well as the pro- and prepro- forms of such protease variants. The prepro- forms are the preferred construction since this facilitates the expression, secretion and maturation of the protease variants.

"Prosequence" refers to a sequence of amino acids bound to the N-terminal portion of the mature form of a protease which when removed results in the appearance of the "mature" form of the protease. Many proteolytic enzymes are found in nature as translational proenzyme products and, in the absence of post-translational processing, are expressed in this fashion. A preferred prosequence for producing protease variants is the putative prosequence of *Bacillus amyloliquefaciens* subtilisin, although other protease prosequences may be used.

A "signal sequence" or "presequence" refers to any sequence of amino acids bound to the N-terminal portion of a protease or to the N-terminal portion of a proprotease which may participate in the secretion of the mature or pro forms of the protease. This definition of signal sequence is a functional one, meant to include all those amino acid sequences encoded by the N-terminal portion of the protease gene which participate in the effectuation of the secretion of protease under native conditions. The present invention utilizes such sequences to effect the secretion of the protease variants as defined herein. One possible signal sequence comprises the first seven amino acid residues of the signal sequence from Bacillus subtilis subtilisin fused to the remainder of the signal sequence of the subtilisin from *Bacillus lentus* (ATCC 21536).

A "prepro" form of a protease variant consists of the mature form of the protease having a prosequence operably linked to the amino terminus of the protease and a "pre" or "signal" sequence operably linked to the amino terminus of the prosequence.

"Expression vector" refers to a DNA construct containing a DNA sequence which is operably linked to a suitable control sequence capable of effecting the expression of said DNA in a suitable host. Such control sequences include a promoter to effect transcription, an optional operator sequence to control such transcription, a sequence encoding suitable mRNA ribosome binding sites and sequences which control termination of transcription and translation. The vector may be a plasmid, a phage particle, or simply a potential genomic insert. Once transformed into a suitable host, the vector may replicate and function independently of the host genome, or may, in some instances, integrate into the genome itself. In the present specification, "plasmid" and "vector" are sometimes used interchangeably as the plasmid is the most commonly used form of vector at present. However, the invention is intended to include such other forms of expression vectors which serve equivalent functions and which are, or become, known in the art.

The "host cells" used in the present invention generally are procaryotic or eucaryotic hosts which preferably have been manipulated by the methods disclosed in U.S. Pat. No. 4,760,025 (RE 34,606) to render them incapable of secreting enzymatically active endoprotease. A preferred host cell for expressing protease is the Bacillus strain BG2036 which is deficient in enzymatically active neutral protease and alkaline protease (subtilisin). The construction of strain BG2036 is described in detail in U.S. Pat. No. 5,264,366. Other host cells for expressing protease include *Bacillus subtilis* 1168 (also described in U.S. Pat. No. 4,760,025 (RE 34,606) and U.S. Pat. No. 5,264,366, the disclosure of which are incorporated herein by reference), as well as any suitable Bacillus strain such as *B. licheniformis, B. lentus,* etc.

Host cells are transformed or transfected with vectors constructed using recombinant DNA techniques. Such transformed host cells are capable of either replicating vectors encoding the protease variants or expressing the desired protease variant. In the case of vectors which encode the pre- or prepro-form of the protease variant, such variants, when expressed, are typically secreted from the host cell into the host cell medium.

"Operably linked", when describing the relationship between two DNA regions, simply means that they are functionally related to each other. For example, a presequence is operably linked to a peptide if it functions as a signal sequence, participating in the secretion of the mature form of the protein most probably involving cleavage of the signal sequence. A promoter is operably linked to a coding sequence if it controls the transcription of the sequence; a ribosome binding site is operably linked to a coding sequence if it is positioned so as to permit translation.

The genes encoding the naturally-occurring precursor protease may be obtained in accord with the general methods known to those skilled in the art. The methods generally comprise synthesizing labeled probes having putative sequences encoding regions of the protease of interest, preparing genomic libraries from organisms expressing the protease, and screening the libraries for the gene of interest by hybridization to the probes. Positively hybridizing clones are then mapped and sequenced.

The cloned protease is then used to transform a host cell in order to express the protease. The protease gene is then ligated into a high copy number plasmid. This plasmid replicates in hosts in the sense that it contains the well-known elements necessary for plasmid replication: a promoter operably linked to the gene in question (which may be supplied as the gene's own homologous promoter if it is recognized, i.e., transcribed, by the host), a transcription termination and polyadenylation region (necessary for stability of the mRNA transcribed by the host from the protease gene in certain eucaryotic host cells) which is exogenous or is supplied by the endogenous terminator region of the protease gene and, desirably, a selection gene such as an antibiotic resistance gene that enables continuous cultural maintenance of plasmid-infected host cells by growth in antibiotic-containing media. High copy number plasmids also contain an origin of replication for the host, thereby enabling large numbers of plasmids to be generated in the cytoplasm without chromosomal limitations. However, it is within the scope herein to integrate multiple copies of the protease gene into host genome. This is facilitated by procaryotic and eucaryotic organisms which are particularly susceptible to homologous recombination.

In one embodiment, the gene can be a natural gene such as that from *B. lentus* or *B. amyloliquefaciens*. Alternatively, a synthetic gene encoding a naturally-occurring or mutant precursor protease may be produced. In such an approach, the DNA and/or amino acid sequence of the precursor protease is determined. Multiple, overlapping synthetic single-stranded DNA fragments are thereafter synthesized, which upon hybridization and ligation produce a synthetic DNA encoding the precursor protease. An example of synthetic gene construction is set forth in Example 3 of U.S. Pat. No. 5,204,015, the disclosure of which is incorporated herein by reference.

Once the naturally-occurring or synthetic precursor protease gene has been cloned, a number of modifications are undertaken to enhance the use of the gene beyond synthesis of the naturally-occurring precursor protease. Such modifications include the production of recombinant proteases as disclosed in U.S. Pat. No. 4,760,025 (RE 34,606) and EPO Publication No. 0 251 446 and the production of protease variants described herein.

The following cassette mutagenesis method may be used to facilitate the construction of the protease variants of the present invention, although other methods may be used. First, the naturally-occurring gene encoding the protease is obtained and sequenced in whole or in part. Then the sequence is scanned for a point at which it is desired to make a mutation (deletion, insertion or substitution) of one or more amino acids in the encoded enzyme. The sequences flanking this point are evaluated for the presence of restriction sites for replacing a short segment of the gene with an oligonucleotide pool which when expressed will encode various mutants. Such restriction sites are preferably unique sites within the protease gene so as to facilitate the replacement of the gene segment. However, any convenient restriction site which is not overly redundant in the protease gene may be used, provided the gene fragments generated by restriction digestion can be reassembled in proper sequence. If restriction sites are not present at locations within a convenient distance from the selected point (from 10 to 15 nucleotides), such sites are generated by substituting nucleotides in the gene in such a fashion that neither the reading frame nor the amino acids encoded are changed in the final construction. Mutation of the gene in order to change its sequence to conform to the desired sequence is accomplished by M13 primer extension in accord with generally known methods. The task of locating suitable flanking regions and evaluating the needed changes to arrive at two convenient restriction site sequences is made routine by the redundancy of the genetic code, a restriction enzyme map of the gene and the large number of different restriction enzymes. Note that if a convenient flanking restriction site is available, the above method need be used only in connection with the flanking region which does not contain a site.

Once the naturally-occurring DNA or synthetic DNA is cloned, the restriction sites flanking the positions to be mutated are digested with the cognate restriction enzymes and a plurality of end termini-complementary oligonucleotide cassettes are ligated into the gene. The mutagenesis is simplified by this method because all of the oligonucleotides can be synthesized so as to have the same restriction sites, and no synthetic linkers are necessary to create the restriction sites.

In one aspect of the invention, the objective is to secure a variant protease having altered allergenic potential as compared to the precursor protease, since decreasing such potential enables safer use of the enzyme. While the instant invention is useful to lower allergenic potential, the mutations specified herein may be utilized in combination with mutations known in the art to result altered thermal stability and/or altered substrate specificity, modified activity or altered alkaline stability as compared to the precursor.

Accordingly, the present invention is directed to altering the capability of the T-cell epitope which includes residue positions 170–173 in *Bacillus lentus* to induce T-cell proliferation. One particularly preferred embodiment of the invention comprises making modification to either one or all of R170D, Y171Q and/or N173D. Similarly, as discussed in detail above, it is believed that the modification of the corresponding residues in any protease will result in a the neutralization of a key T-cell epitope in that protease. Thus, in combination with the presently disclosed mutations in the region corresponding to amino acid residues 170–173, substitutions at positions corresponding to N76D/S103A/V104I/G159D optionally in combination with one or more substitutions selected from the group consisting of positions corresponding to V68A, T213R, A232V, Q236H, Q245R, and T260A of *Bacillus amyloliquefaciens* subtilisin may be used, in addition to decreasing the allergenic potential of the variant protease of the invention, to modulate overall stability and/or proteolytic activity of the enzyme. Similarly, the substitutions provided herein may be combined with mutation at the Asparagine (N) in *Bacillus lentus* subtilisin at equivalent position +76 to Aspartate (D) in combination with the mutations S103A/V104I/G159D and optionally in combination with one or more substitutions selected from the group consisting of positions corresponding to V68A, T213R, A232V, Q236H, Q245R, and T260A of *Bacillus amyloliquefaciens* subtilisin, to produce enhanced stability and/or enhanced activity of the resulting mutant enzyme.

The most preferred embodiments of the invention include the following specific combinations of substituted residues corresponding to positions: N76D/S103A/V104I/G159D/K170D/Y171Q/S173D; V68A/N76D/S103A/V104I/G159D/K170D/Y171Q/S173D/Q236H; V68A/N76D/S103A/V104I/G159D/K170D/Y171Q/S173D/Q236H/Q245R; V68A/N76D/S103A/V104I/G159D/K170D/Y171Q/S173D/A232V/Q236H/Q245R; and V68A/N76D/S103A/V104I/G159D/K170D/Y171Q/S173D/T213R/A232V/Q236H/Q245R/T260A of *Bacillus amyloliquefaciens* subtilisin. These substitutions are preferably made in *Bacillus lentus* (recombinant or native-type) subtilisin, although the substitutions may be made in any Bacillus protease.

Based on the screening results obtained with the variant proteases, the noted mutations noted above in *Bacillus amyloliquefaciens* subtilisin are important to the proteolytic activity, performance and/or stability of these enzymes and the cleaning or wash performance of such variant enzymes.

Many of the protease variants of the invention are useful in formulating various detergent compositions. A number of known compounds are suitable surfactants useful in compositions comprising the protease mutants of the invention. These include nonionic, anionic, cationic, anionic or zwitterionic detergents, as disclosed in U.S. Pat. No. 4,404,128 to Barry J. Anderson and U.S. Pat. No. 4,261,868 to Jiri Flora, et al. A suitable detergent formulation is that described in Example 7 of U.S. Pat. No. 5,204,015 (previously incorporated by reference). The art is familiar with the different formulations which can be used as cleaning compositions. In addition to typical cleaning compositions, it is readily understood that the protease variants of the present invention may be used for any purpose that native or wild-type proteases are used. Thus, these variants can be used, for example, in bar or liquid soap applications, dishcare formulations, contact lens cleaning solutions or products, peptide hydrolysis, waste treatment, textile applications, as fusion-cleavage enzymes in protein production, etc. The variants of the present invention may comprise, in addition to decreased allergenicity, enhanced performance in a detergent composition (as compared to the precursor). As used herein, enhanced performance in a detergent is defined as increasing cleaning of certain enzyme sensitive stains such as grass or blood, as determined by usual evaluation after a standard wash cycle.

Proteases of the invention can be formulated into known powdered and liquid detergents having pH between 6.5 and 12.0 at levels of about 0.01 to about 5% (preferably 0.1% to 0.5%) by weight. These detergent cleaning compositions can also include other enzymes such as known proteases, amylases, cellulases, lipases or endoglycosidases, as well as builders and stabilizers.

The addition of proteases of the invention to conventional cleaning compositions does not create any special use limitation. In other words, any temperature and pH suitable for the detergent is also suitable for the present compositions as long as the pH is within the above range, and the temperature is below the described protease's denaturing temperature. In addition, proteases of the invention can be used in a cleaning composition without detergents, again either alone or in combination with builders and stabilizers.

The variant proteases of the present invention can be included in animal feed such as part of animal feed additives as described in, for example, U.S. Pat. No. 5,612,055; U.S. Pat. No. 5,314,692; and U.S. Pat. No. 5,147,642.

One aspect of the invention is a composition for the treatment of a textile that includes variant proteases of the present invention. The composition can be used to treat for example silk or wool as described in publications such as RD 216,034; EP 134,267; U.S. Pat. No. 4,533,359; and EP 344,259.

The following is presented by way of example and is not to be construed as a limitation to the scope of the claims.

The variants can be screened for proteolytic activity according to methods well known in the art. Preferred protease variants include multiple substitutions at positions corresponding to: N76D/S103A/V141I/G159D/K170D/Y171Q/S173D; V68A/N76D/S103A/V104I/G159D/K170D/Y171Q/S173D/Q236H; V68A/N76D/S103A/V104I/G159D/K170D/Y171Q/S173D/Q236H/Q245R; V68A/N76D/S103A/V104I/G159D/K170D/Y171Q/S173D/A232V/Q236H/Q245R; and V68A/N76D/S103A/V104I/G159D/K170D/Y171Q/S173D/T213R/A232V/Q236H/Q245 R/T260A of *Bacillus amyloliquefaciens* subtilisin.

All publications and patents referenced herein are hereby incorporated by reference in their entirety.

EXAMPLES

Example 1

Assay for the Identification of Peptide T-Cell Epitopes Using Naive Human T-Cells Fresh human peripheral blood cells were collected from "naive" humans, i.e., persons not known to be exposed to or sensitized to *Bacillus lentus* protease, for determination of antigenic epitopes in protease from *Bacillus lentus* and human subtilisin. Naive humans is intended to mean that the individual is not known to have been exposed to or developed a reaction to protease in the past. Peripheral mononuclear blood cells (stored at room temperature, no older than 24 hours) were prepared for use as follows: Approximately 30 mls of a solution of buffy coat preparation from one unit of whole blood was brought to 50 ml with Dulbecco's phosphate buffered solution (DPBS) and split into two tubes. The samples were underlaid with 12.5 ml of room temperature lymphoprep density separation media (Nycomed density 1.077 g/ml). The tubes were centrifuged for thirty minutes at 600 G. The interface of the two phases was collected, pooled and washed in DPBS. The cell density of the resultant solution was measured by hemocytometer. Viability was measured by trypan blue exclusion.

From the resulting solution, a differentiated dendritic cell culture was prepared from the peripheral blood mononuclear cell sample having a density of $10^8$ cells per 75 ml culture flask in a solution as follows:

(1) 50 ml of serum free AIM V media (Gibco) was supplemented with a 1:100 dilution beta-mercaptoethanol (Gibco). The flasks were laid flat for two hours at 37° C. in 5% $CO_2$ to allow adherence of monocytes to the flask wall.

(2) Differentiation of the monocyte cells to dendritic cells was as follows: nonadherent cells were removed and the resultant adherent cells (monocytes) combined with 30 ml of AIM V, 800 units/ml of GM-CSF (Endogen) and 500 units/ml of IL4 (Endogen); the resulting mixture was cultured for 5 days under conditions at 37° C. in 5% $CO_2$. After five days, the cytokine TNFα (Endogen) was added to 0.2 units/ml, and the cytokine IL-1α (Endogen) was added to a final concentration of 50 units/ml and the mixture incubated at 37° C. in 5% $CO_2$ for two more days.

(3) On the seventh day, Mitomycin C was added to a concentration of 50 microgram/ml was added to stop growth of the now differentiated dendritic cell culture. The solution was incubated for 60 minutes at 37° C. in 5% $CO_2$. Dendritic cells were collected by gently scraping the adherent cells off the bottom of the flask with a cell scraper. Adherent and non-adherent cells were then centrifuged at 600 G for 5 minutes, washed in DPBS and counted.

(4) The prepared dendritic cells were placed into a 96 well round bottom array at $2 \times 10^4$/well in 100 microliter total volume of AIM V media.

CD4+ T cells were prepared from frozen aliquots of the peripheral blood cell samples used to prepare the dendritic cells using the human CD4+ Cellect Kit (Biotex) as per the manufacturers instructions with the following modifications: the aliquots were thawed and washed such that approximately $10^8$ cells will be applied per Cellect column; the cells were resuspended in 4 ml DPBS and 1 ml of the Cell reagent from the Cellect Kit, the solution maintained at room temperature for 20 minutes. The resultant solution was centrifuged for five minutes at 600 G at room temperature and the pellet resuspended in 2 ml of DPBS and applied to the Cellect columns. The effluent from the columns was collected in 2% human serum in DPBS. The resultant CD4+ cell solution was centrifuged, resuspended in AIMV media and the density counted.

The CD4+ T-cell suspension was resuspended to a count of $2 \times 10^6$/ml in AIM V media to facilitate efficient manipulation of the 96 well plate.

Peptide antigen is prepared from a 1M stock solution in DMSO by dilution in AIM V media at a 1:10 ratio. 10 microliters of the stock solution is placed in each well of the 96 well plate containing the differentiated dendritic cells. 100 microliter of the diluted CD4+ T-cell solution as prepared above is further added to each well. Useful controls include diluted DMSO blanks, and tetanus toxoid positive controls.

The final concentrations in each well, at 210 microliter total volume are as follows:
2×10⁴ CD4+
2×10⁵ dendtritic cells (R:S of 10:1)
5 mM peptide

Example 2

Identification of T-Cell Epitopes in Protease from *Bacillus lentus* and Human subtilisin Peptides for use in the assay described in Example 1 were prepared based on the *Bacillus lentus* and human subtilisin amino acid sequence. Peptide antigens were designed as follows. From the full length amino acid sequence of either human subtilisin or *Bacillus lentus* protease provided in FIG. 1, 15 mers were synthetically prepared, each 15 mer overlapping with the previous and the subsequent 15 mer except for three residues.

Peptides used correspond to amino acid residue strings in *Bacillus lentus* as provided in FIG. 8, and peptides correspond to amino acid residues in human subtilisin as provided in FIG. 7. The peptides used corresponding to the proteases is provided in FIG. 6. All tests were performed at least in duplicate. All tests reported displayed robust positive control responses to the antigen tetanus toxoid. Responses were averaged within each experiment, then normalized to the baseline response. A positive event was recorded if the response was at least 3 times the baseline response.

The immunogenic response (i.e., T-cell proliferation) to the prepared peptides from human subtilisin and *Bacillus lentus* was tallied and is provided in FIGS. 4 and 5, respectively. T-cell proliferation was measured by the incorporated tritium method. The results shown in FIGS. 4 and 5 as a comparison of the immunogenic additive response in 10 individuals (FIG. 4) and 16 individuals (FIG. 5) to the various peptides. Response is indicated as the added response wherein 1.0 equals a baseline response for each sample. Thus, in FIG. 4, a reading of 10.0 or less is the baseline response and in FIG. 5 a reading of 16.0 or less the baseline response.

As indicated in FIGS. 4 and 5, the immunogenic response of the naive blood samples from unsensitized individuals showed a marked allergenic response at the peptide fragment from *Bacillus lentus* corresponding to residues 170–173 of *Bacillus amyloliquefaciens* protease. As expected, the corresponding fragment in human subtilisin evokes merely baseline response.

FIG. 9 shows the T-cell response to peptides derived from *Bacillus lentus* protease in a sample taken from an individual known to be hypersensitive to *Bacillus lentus* protease. Peptide E05 represents the region corresponding to 170–173 in protease from *Bacillus amyloliquefaciens*. As shown in FIG. 9, the hypersensitive individual was highly responsive to the T-cell epitope represented by the peptide E05. This result confirms that, by practicing the assay according to the invention, it is possible to predict the major epitopes identified by the T-cells of a hypersensitive individual.

FIG. 10 shows the T-cell response to various alanine substitutions in the E05 peptide derived from *Bacillus lentus* protease in a sample taken from an individual known to be hypersensitive to *Bacillus lentus* protease. Alanine substitutions were used as substitutions for the purpose of determining the role of any specific residue within the epitope. The legend of FIG. 10 refers to the position of the peptide in which an alanine was substituted, i.e., in peptide E06 (sequence GSISYPARYANAMAV) (residues 157–171 at SEQ ID NO: 5), G to A=2, S to A=3, I to A=4, S to A=5,Y to A=6, P to A=7, R to A=8,Y to A=9, N to A=10,M to A=11 and V to A=12. As indicated in FIG. 10, substitution of either of the residues R170A, Y171A and/or N173A in protease from *Bacillus lentus* results in dramatically reduced response in the hypersensitive individual's blood sample.

From these results, it is apparent that the residues 170, 171 and 173 are critical for T-cell response within this peptide. Accordingly, it is further apparent that these residues are largely responsible for the initiation of allergic reaction within the protease from *Bacillus lentus*.

We claim:

1. A protease variant comprising a substitution made at Y171Q and at one or both of the positions in a precursor protease corresponding to K170D and/or S173D of *Bacillus amyloliquefaciens* subtilisin.

2. A protease variant according to claim 1, comprising combined substitution sets selected from the group consisting of positions corresponding to K170D/Y171Q/S173D; N76D/S103A/V104I/G159D/K170D/Y171Q/S173D; V68A/N76D/S103A/V104I/G159D/K170D/Y171Q/S173D/Q236H; V68A/N76D/S103A/V104I/G159D/K170D/Y171Q/S173D/Q236H/Q245R; V68A/N76D/S103A/V104I/G159D/K170D/Y171Q/S173D/A232V/Q236H/Q245R; and V68A/N76D/S103A/V104I/G159D/K170D/Y171S/S173D/T213R/A232V/Q236H/Q245R/T260A wherein K170D/Y171Q/S173D positions are found in *Bacilus amyloliquefaciens* subtilisin and the remaining positions are found in *Bacillus lentis* subtilisin.

3. A protease variant comprising a substitution made at one or both of the positions in a precursor protease corresponding to K170D and/or S173D of *Bacillus amyloliquefaciens* subtilisin.

4. A protease variant according to claim 3, comprising combined substitution sets selected from the group consisting of positions corresponding to K170D/S173D;N76D/S103A/V104I/G159D/K170D/S173D; V68A/N76D/S103A/V104I/G159D/K170D/S173D/Q236H; V68A/N76D/S103A/V104I/G159D/K170D/S173D/Q236H/Q245R; V68A/N76D/S103A/V104I/G159D/K170D/S173D/A232V/Q236H/Q245R; and V68A/N76D/S103A/V104I/G159D/K170D/S173D/T213R/A232V/Q236H/Q245R/T260A; wherein K170D/S173D positions are found in *Bacilus amyloliquefaciens* subtilisin and the remaining positions are found in *Bacillus lentis* subtilisin.

5. The protease variant according to claim 1 or 3, further comprising a substitution at one or more positions in a precursor protease equivalent to those selected from the group consisting of N76D, S103A, V104I, G159D, V68A, T213R, A232V, Q236H, Q245R, and T260A of *Bacillus lentis* subtilisin.

6. The protease variant according to claim 5 which is derived from a *Bacillus subtilisin*.

7. The protease variant according to claim 6 which is derived from *Bacillus lentus* subtilisin or *Bacillus amyloliquefaciens* subtilisin.

8. A cleaning composition comprising the protease variant of claim 1 or 3.

9. An animal feed composition comprising the protease variant of claim 1 or 3.

10. A composition comprising the protease variant of claim 1 or 3 for treating a textile.

* * * * *

SEQUENCE LISTING

```
<160> NUMBER OF SEQ ID NOS:  7

<210> SEQ ID NO 1
<211> LENGTH: 1494
<212> TYPE: DNA
<213> ORGANISM: Bacillus amyloliquefaciens
<220> FEATURE:
<221> NAME/KEY: CDS
<222> LOCATION: (96)..(1244)
<221> NAME/KEY: mat_peptide
<222> LOCATION: (417)..(1241)

<400> SEQUENCE: 1
ggtctactaa aatattattc catactatac aattaataca cagaataatc tgtctattgg      60
ttattctgca aatgaaaaaa aggagaggat aaaga gtg aga ggc aaa aaa gta        113
                                       Val Arg Gly Lys Lys Val
                                          -105 tgg atc agt ttg ctg ttt gct tta gcg tta atc ttt acg atg gcg ttc      161
Trp Ile Ser Leu Leu Phe Ala Leu Ala Leu Ile Phe Thr Met Ala Phe
    -100                 -95                 -90 ggc agc aca tcc tct gcc cag gcg gca ggg aaa tca aac ggg gaa aag      209
Gly Ser Thr Ser Ser Ala Gln Ala Ala Gly Lys Ser Asn Gly Glu Lys
```

```
            -85                 -80                 -75                 -70
aaa tat att gtc ggg ttt aaa cag aca atg agc acg atg agc gcc gct           257
Lys Tyr Ile Val Gly Phe Lys Gln Thr Met Ser Thr Met Ser Ala Ala
            -65                 -60                 -55 aag aag aaa gat gtc att tct gaa aaa ggc ggg aaa gtg caa aag caa           305
Lys Lys Lys Asp Val Ile Ser Glu Lys Gly Gly Lys Val Gln Lys Gln
            -50                 -45                 -40 ttc aaa tat gta gac gca gct tca gct aca tta aac gaa aaa gct gta           353
Phe Lys Tyr Val Asp Ala Ala Ser Ala Thr Leu Asn Glu Lys Ala Val
            -35                 -30                 -25 aaa gaa ttg aaa aaa gac ccg agc gtc gct tac gtt gaa gaa gat cac           401
Lys Glu Leu Lys Lys Asp Pro Ser Val Ala Tyr Val Glu Glu Asp His
            -20                 -15                 -10 gta gca cat gcg tac gcg cag tcc gtg cct tac ggc gta tca caa att           449
Val Ala His Ala Tyr Ala Gln Ser Val Pro Tyr Gly Val Ser Gln Ile
 -5              -1   1                   5                  10 aaa gcc cct gct ctg cac tct caa ggc tac act gga tca aat gtt aaa           497
Lys Ala Pro Ala Leu His Ser Gln Gly Tyr Thr Gly Ser Asn Val Lys
             15                  20                  25 gta gcg gtt atc gac agc ggt atc gat tct tct cat cct gat tta aag           545
Val Ala Val Ile Asp Ser Gly Ile Asp Ser Ser His Pro Asp Leu Lys
             30                  35                  40 gta gca ggc gga gcc agc atg gtt cct tct gaa aca aat cct ttc caa           593
Val Ala Gly Gly Ala Ser Met Val Pro Ser Glu Thr Asn Pro Phe Gln
 45                  50                  55 gac aac aac tct cac gga act cac gtt gcc ggc aca gtt gcg gct ctt           641
Asp Asn Asn Ser His Gly Thr His Val Ala Gly Thr Val Ala Ala Leu
 60                  65                  70                  75 aat aac tca atc ggt gta tta ggc gtt gcg cca agc gca tca ctt tac           689
Asn Asn Ser Ile Gly Val Leu Gly Val Ala Pro Ser Ala Ser Leu Tyr
             80                  85                  90 gct gta aaa gtt ctc ggt gct gac ggt tcc ggc caa tac agc tgg atc           737
Ala Val Lys Val Leu Gly Ala Asp Gly Ser Gly Gln Tyr Ser Trp Ile
             95                 100                 105 att aac gga atc gag tgg gcg atc gca aac aat atg gac gtt att aac           785
Ile Asn Gly Ile Glu Trp Ala Ile Ala Asn Asn Met Asp Val Ile Asn
            110                 115                 120 atg agc ctc ggc gga cct tct ggt tct gct gct tta aaa gcg gca gtt           833
Met Ser Leu Gly Gly Pro Ser Gly Ser Ala Ala Leu Lys Ala Ala Val
            125                 130                 135 gat aaa gcc gtt gca tcc ggc gtc gta gtc gtt gcg gca gcc ggt aac           881
Asp Lys Ala Val Ala Ser Gly Val Val Val Ala Ala Ala Gly Asn
140                 145                 150                 155 gaa ggc act tcc ggc agc tca agc aca gtg ggc tac cct ggt aaa tac           929
Glu Gly Thr Ser Gly Ser Ser Thr Val Gly Tyr Pro Gly Lys Tyr
                160                 165                 170 cct tct gtc att gca gta ggc gct gtt gac agc agc aac caa aga gca           977
Pro Ser Val Ile Ala Val Gly Ala Val Asp Ser Ser Asn Gln Arg Ala
            175                 180                 185 tct ttc tca agc gta gga cct gag ctt gat gtc atg gca cct ggc gta          1025
Ser Phe Ser Ser Val Gly Pro Glu Leu Asp Val Met Ala Pro Gly Val
            190                 195                 200 tct atc caa agc acg ctt cct gga aac aaa tac ggg gcg tac aac ggt          1073
Ser Ile Gln Ser Thr Leu Pro Gly Asn Lys Tyr Gly Ala Tyr Asn Gly
            205                 210                 215 acg tca atg gca tct ccg cac gtt gcc gga gcg gct gct ttg att ctt          1121
Thr Ser Met Ala Ser Pro His Val Ala Gly Ala Ala Ala Leu Ile Leu
220                 225                 230                 235 tct aag cac ccg aac tgg aca aac act caa gtc cgc agc agt tta gaa          1169
```

-continued

```
Ser Lys His Pro Asn Trp Thr Asn Thr Gln Val Arg Ser Ser Leu Glu
            240                 245                 250 aac acc act aca aaa ctt ggt gat tct ttc tac tat gga aaa ggg ctg    1217
Asn Thr Thr Thr Lys Leu Gly Asp Ser Phe Tyr Tyr Gly Lys Gly Leu
            255                 260                 265 atc aac gta cag gcg gca gct cag taa aacataaaaa accggccttg          1264
Ile Asn Val Gln Ala Ala Ala Gln
            270             275 gccccgccgg ttttttattt ttcttcctcc gcatgttcaa tccgctccat aatcgacgga   1324
tggctccctc tgaaaatttt aacgagaaac ggcgggttga cccggctcag tcccgtaacg   1384
gccaagtcct gaaacgtctc aatcgccgct tcccggtttc cggtcagctc aatgccgtaa   1444
cggtcggcgg cgttttcctg ataccgggag acggcattcg taatcggatc              1494

<210> SEQ ID NO 2
<211> LENGTH: 382
<212> TYPE: PRT
<213> ORGANISM: Bacillus amyloliquefaciens

<400> SEQUENCE: 2

Val Arg Gly Lys Lys Val Trp Ile Ser Leu Leu Phe Ala Leu Ala Leu
 1               5                  10                  15

Ile Phe Thr Met Ala Phe Gly Ser Thr Ser Ser Ala Gln Ala Ala Gly
            20                  25                  30

Lys Ser Asn Gly Glu Lys Lys Tyr Ile Val Gly Phe Lys Gln Thr Met
            35                  40                  45

Ser Thr Met Ser Ala Ala Lys Lys Asp Val Ile Ser Glu Lys Gly
        50                  55                  60

Gly Lys Val Gln Lys Gln Phe Lys Tyr Val Asp Ala Ala Ser Ala Thr
65                  70                  75                  80

Leu Asn Glu Lys Ala Val Lys Glu Leu Lys Lys Asp Pro Ser Val Ala
                85                  90                  95

Tyr Val Glu Glu Asp His Val Ala His Ala Tyr Ala Gln Ser Val Pro
            100                 105                 110

Tyr Gly Val Ser Gln Ile Lys Ala Pro Ala Leu His Ser Gln Gly Tyr
        115                 120                 125

Thr Gly Ser Asn Val Lys Val Ala Val Ile Asp Ser Gly Ile Asp Ser
    130                 135                 140

Ser His Pro Asp Leu Lys Val Ala Gly Gly Ala Ser Met Val Pro Ser
145                 150                 155                 160

Glu Thr Asn Pro Phe Gln Asp Asn Asn Ser His Gly Thr His Val Ala
                165                 170                 175

Gly Thr Val Ala Ala Leu Asn Asn Ser Ile Gly Val Leu Gly Val Ala
            180                 185                 190

Pro Ser Ala Ser Leu Tyr Ala Val Lys Val Leu Gly Ala Asp Gly Ser
        195                 200                 205

Gly Gln Tyr Ser Trp Ile Ile Asn Gly Ile Glu Trp Ala Ile Ala Asn
    210                 215                 220

Asn Met Asp Val Ile Asn Met Ser Leu Gly Gly Pro Ser Gly Ser Ala
225                 230                 235                 240

Ala Leu Lys Ala Ala Val Asp Lys Ala Val Ala Ser Gly Val Val Val
                245                 250                 255

Val Ala Ala Ala Gly Asn Glu Gly Thr Ser Gly Ser Ser Ser Thr Val
            260                 265                 270

Gly Tyr Pro Gly Lys Tyr Pro Ser Val Ile Ala Val Gly Ala Val Asp
```

```
                275                 280                 285
Ser Ser Asn Gln Arg Ala Ser Phe Ser Ser Val Gly Pro Glu Leu Asp
    290                 295                 300

Val Met Ala Pro Gly Val Ser Ile Gln Ser Thr Leu Pro Gly Asn Lys
305                 310                 315                 320

Tyr Gly Ala Tyr Asn Gly Thr Ser Met Ala Ser Pro His Val Ala Gly
                325                 330                 335

Ala Ala Ala Leu Ile Leu Ser Lys His Pro Asn Trp Thr Asn Thr Gln
                340                 345                 350

Val Arg Ser Ser Leu Glu Asn Thr Thr Lys Leu Gly Asp Ser Phe
                355                 360                 365

Tyr Tyr Gly Lys Gly Leu Ile Asn Val Gln Ala Ala Gln
                370                 375                 380

<210> SEQ ID NO 3
<211> LENGTH: 275
<212> TYPE: PRT
<213> ORGANISM: Bacillus subtilis

<400> SEQUENCE: 3

Ala Gln Ser Val Pro Tyr Gly Ile Ser Gln Ile Lys Ala Pro Ala Leu
1               5                   10                  15

His Ser Gln Gly Tyr Thr Gly Ser Asn Val Lys Val Ala Val Ile Asp
                20                  25                  30

Ser Gly Ile Asp Ser Ser His Pro Asp Leu Asn Val Arg Gly Gly Ala
            35                  40                  45

Ser Phe Val Pro Ser Glu Thr Asn Pro Tyr Gln Asp Gly Ser Ser His
        50                  55                  60

Gly Thr His Val Ala Gly Thr Ile Ala Ala Leu Asn Asn Ser Ile Gly
65                  70                  75                  80

Val Leu Gly Val Ser Pro Ser Ala Ser Leu Tyr Ala Val Lys Val Leu
                85                  90                  95

Asp Ser Thr Gly Ser Gly Gln Tyr Ser Trp Ile Ile Asn Gly Ile Glu
                100                 105                 110

Trp Ala Ile Ser Asn Asn Met Asp Val Ile Asn Met Ser Leu Gly Gly
            115                 120                 125

Pro Thr Gly Ser Thr Ala Leu Lys Thr Val Val Asp Lys Ala Val Ser
130                 135                 140

Ser Gly Ile Val Val Ala Ala Ala Ala Gly Asn Glu Gly Ser Ser Gly
145                 150                 155                 160

Ser Thr Ser Thr Val Gly Tyr Pro Ala Lys Tyr Pro Ser Thr Ile Ala
                165                 170                 175

Val Gly Ala Val Asn Ser Ser Asn Gln Arg Ala Ser Phe Ser Ser Ala
                180                 185                 190

Gly Ser Glu Leu Asp Val Met Ala Pro Gly Val Ser Ile Gln Ser Thr
            195                 200                 205

Leu Pro Gly Gly Thr Tyr Gly Ala Tyr Asn Gly Thr Ser Met Ala Thr
        210                 215                 220

Pro His Val Ala Gly Ala Ala Ala Leu Ile Leu Ser Lys His Pro Thr
225                 230                 235                 240

Trp Thr Asn Ala Gln Val Arg Asp Arg Leu Glu Ser Thr Ala Thr Tyr
                245                 250                 255

Leu Gly Asn Ser Phe Tyr Tyr Gly Lys Gly Leu Ile Asn Val Gln Ala
                260                 265                 270
```

-continued

```
Ala Ala Gln
        275

<210> SEQ ID NO 4
<211> LENGTH: 274
<212> TYPE: PRT
<213> ORGANISM: Bacillus licheniformis

<400> SEQUENCE: 4

Ala Gln Thr Val Pro Tyr Gly Ile Pro Leu Ile Lys Ala Asp Lys Val
  1               5                  10                  15

Gln Ala Gln Gly Phe Lys Gly Ala Asn Val Lys Val Ala Val Leu Asp
             20                  25                  30

Thr Gly Ile Gln Ala Ser His Pro Asp Leu Asn Val Val Gly Gly Ala
         35                  40                  45

Ser Phe Val Ala Gly Glu Ala Tyr Asn Thr Asp Gly Asn Gly His Gly
     50                  55                  60

Thr His Val Ala Gly Thr Val Ala Ala Leu Asp Asn Thr Thr Gly Val
 65                  70                  75                  80

Leu Gly Val Ala Pro Ser Val Ser Leu Tyr Ala Val Lys Val Leu Asn
                 85                  90                  95

Ser Ser Gly Ser Gly Ser Tyr Ser Gly Ile Val Ser Gly Ile Glu Trp
            100                 105                 110

Ala Thr Thr Asn Gly Met Asp Val Ile Asn Met Ser Leu Gly Gly Ala
        115                 120                 125

Ser Gly Ser Thr Ala Met Lys Gln Ala Val Asp Asn Ala Tyr Ala Arg
    130                 135                 140

Gly Val Val Val Ala Ala Ala Gly Asn Ser Gly Asn Ser Gly Ser
145                 150                 155                 160

Thr Asn Thr Ile Gly Tyr Pro Ala Lys Tyr Asp Ser Val Ile Ala Val
                165                 170                 175

Gly Ala Val Asp Ser Asn Ser Asn Arg Ala Ser Phe Ser Ser Val Gly
            180                 185                 190

Ala Glu Leu Glu Val Met Ala Pro Gly Ala Gly Val Tyr Ser Thr Tyr
        195                 200                 205

Pro Thr Asn Thr Tyr Ala Thr Leu Asn Gly Thr Ser Met Ala Ser Pro
    210                 215                 220

His Val Ala Gly Ala Ala Ala Leu Ile Leu Ser Lys His Pro Asn Leu
225                 230                 235                 240

Ser Ala Ser Gln Val Arg Asn Arg Leu Ser Ser Thr Ala Thr Tyr Leu
                245                 250                 255

Gly Ser Ser Phe Tyr Tyr Gly Lys Gly Leu Ile Asn Val Glu Ala Ala
            260                 265                 270

Ala Gln

<210> SEQ ID NO 5
<211> LENGTH: 269
<212> TYPE: PRT
<213> ORGANISM: Bacillus lentus

<400> SEQUENCE: 5

Ala Gln Ser Val Pro Trp Gly Ile Ser Arg Val Gln Ala Pro Ala Ala
  1               5                  10                  15

His Asn Arg Gly Leu Thr Gly Ser Gly Val Lys Val Ala Val Leu Asp
             20                  25                  30

Thr Gly Ile Ser Thr His Pro Asp Leu Asn Ile Arg Gly Gly Ala Ser
```

-continued

```
                35                  40                  45
Phe Val Pro Gly Glu Pro Ser Thr Gln Asp Gly Asn Gly His Gly Thr
         50                  55                  60
His Val Ala Gly Thr Ile Ala Ala Leu Asn Asn Ser Ile Gly Val Leu
 65                  70                  75                  80
Gly Val Ala Pro Ser Ala Glu Leu Tyr Ala Val Lys Val Leu Gly Ala
                 85                  90                  95
Ser Gly Ser Gly Ser Val Ser Ser Ile Ala Gln Gly Leu Glu Trp Ala
                100                 105                 110
Gly Asn Asn Gly Met His Val Ala Asn Leu Ser Leu Gly Ser Pro Ser
            115                 120                 125
Pro Ser Ala Thr Leu Glu Gln Ala Val Asn Ser Ala Thr Ser Arg Gly
        130                 135                 140
Val Leu Val Val Ala Ala Ser Gly Asn Ser Gly Ala Gly Ser Ile Ser
145                 150                 155                 160
Tyr Pro Ala Arg Tyr Ala Asn Ala Met Ala Val Gly Ala Thr Asp Gln
                165                 170                 175
Asn Asn Asn Arg Ala Ser Phe Ser Gln Tyr Gly Ala Gly Leu Asp Ile
            180                 185                 190
Val Ala Pro Gly Val Asn Val Gln Ser Thr Tyr Pro Gly Ser Thr Tyr
        195                 200                 205
Ala Ser Leu Asn Gly Thr Ser Met Ala Thr Pro His Val Ala Gly Ala
    210                 215                 220
Ala Ala Leu Val Lys Gln Lys Asn Pro Ser Trp Ser Asn Val Gln Ile
225                 230                 235                 240
Arg Asn His Leu Lys Asn Thr Ala Thr Ser Leu Gly Ser Thr Asn Leu
                245                 250                 255
Tyr Gly Ser Gly Leu Val Asn Ala Glu Ala Ala Thr Arg
            260                 265
```

<210> SEQ ID NO 6
<211> LENGTH: 15
<212> TYPE: PRT
<213> ORGANISM: Unknown
<220> FEATURE:
<223> OTHER INFORMATION: Description of Unknown Organism: Unknown
      Sequence

<400> SEQUENCE: 6

```
Ile Lys Asp Phe His Val Tyr Phe Arg Glu Ser Arg Asp Ala Gly
 1               5                  10                  15
```

<210> SEQ ID NO 7
<211> LENGTH: 1052
<212> TYPE: PRT
<213> ORGANISM: Homo sapiens

<400> SEQUENCE: 7

```
Met Lys Leu Val Asn Ile Trp Leu Leu Leu Val Leu Leu Cys
 1               5                  10                  15
Gly Lys Lys His Leu Gly Asp Arg Leu Glu Lys Lys Ser Phe Glu Lys
            20                  25                  30
Ala Pro Cys Pro Gly Cys Ser His Leu Thr Leu Lys Val Glu Phe Ser
        35                  40                  45
Ser Thr Val Val Glu Tyr Glu Tyr Ile Val Ala Phe Asn Gly Tyr Phe
    50                  55                  60
Thr Ala Lys Ala Arg Asn Ser Phe Ile Ser Ser Ala Leu Lys Ser Ser
```

```
                65                   70                  75                  80
         Glu Val Asp Asn Trp Arg Ile Ile Pro Arg Asn Asn Pro Ser Ser Asp
                                85                  90                  95
         Tyr Pro Ser Asp Phe Glu Val Ile Gln Ile Lys Glu Lys Gln Lys Ala
                           100                 105                 110
         Gly Leu Leu Thr Leu Glu Asp His Pro Asn Ile Lys Arg Val Thr Pro
                           115                 120                 125
         Gln Arg Lys Val Phe Arg Ser Leu Lys Tyr Ala Glu Ser Asp Pro Thr
                           130                 135                 140
         Val Pro Cys Asn Glu Thr Arg Trp Ser Gln Lys Trp Gln Ser Ser Arg
         145                 150                 155                 160
         Pro Leu Arg Arg Ala Ser Leu Ser Leu Gly Ser Gly Phe Trp His Ala
                           165                 170                 175
         Thr Gly Arg His Ser Ser Arg Arg Leu Leu Arg Ala Ile Pro Arg Gln
                           180                 185                 190
         Val Ala Gln Thr Leu Gln Ala Asp Val Leu Trp Gln Met Gly Tyr Thr
                           195                 200                 205
         Gly Ala Asn Val Arg Val Ala Val Phe Asp Thr Gly Leu Ser Glu Lys
                           210                 215                 220
         His Pro His Phe Lys Asn Val Lys Glu Arg Thr Asn Trp Thr Asn Glu
         225                 230                 235                 240
         Arg Thr Leu Asp Asp Gly Leu Gly His Gly Thr Phe Val Ala Gly Val
                           245                 250                 255
         Ile Ala Ser Met Arg Glu Cys Gln Gly Phe Ala Pro Asp Ala Glu Leu
                           260                 265                 270
         His Ile Phe Arg Val Phe Thr Asn Asn Gln Val Ser Tyr Thr Ser Trp
                           275                 280                 285
         Phe Leu Asp Ala Phe Asn Tyr Ala Ile Leu Lys Lys Ile Asp Val Leu
                           290                 295                 300
         Asn Leu Ser Ile Gly Gly Pro Asp Phe Met Asp His Pro Phe Val Asp
         305                 310                 315                 320
         Lys Val Trp Glu Leu Thr Ala Asn Asn Val Ile Met Val Ser Ala Ile
                           325                 330                 335
         Gly Asn Asp Gly Pro Leu Tyr Gly Thr Leu Asn Asn Pro Ala Asp Gln
                           340                 345                 350
         Met Asp Val Ile Gly Val Gly Gly Ile Asp Phe Glu Asp Asn Ile Ala
                           355                 360                 365
         Arg Phe Ser Ser Arg Gly Met Thr Thr Trp Glu Leu Pro Gly Gly Tyr
                           370                 375                 380
         Gly Arg Met Lys Pro Asp Ile Val Thr Tyr Gly Ala Gly Val Arg Gly
         385                 390                 395                 400
         Ser Gly Val Lys Gly Gly Cys Arg Ala Leu Ser Gly Thr Ser Val Ala
                           405                 410                 415
         Ser Pro Val Val Ala Gly Ala Val Thr Leu Leu Val Ser Thr Val Gln
                           420                 425                 430
         Lys Arg Glu Leu Val Asn Pro Ala Ser Met Lys Gln Ala Leu Ile Ala
                           435                 440                 445
         Ser Ala Arg Arg Leu Pro Gly Val Asn Met Phe Glu Gln Gly His Gly
                           450                 455                 460
         Lys Leu Asp Leu Leu Arg Ala Tyr Gln Ile Leu Asn Ser Tyr Lys Pro
         465                 470                 475                 480
         Gln Ala Ser Leu Ser Pro Ser Tyr Ile Asp Leu Thr Glu Cys Pro Tyr
                           485                 490                 495
```

-continued

```
Met Trp Pro Tyr Cys Ser Gln Pro Ile Tyr Tyr Gly Gly Met Pro Thr
            500                 505                 510

Val Val Asn Val Thr Ile Leu Asn Gly Met Gly Val Thr Gly Arg Ile
            515                 520                 525

Val Asp Lys Pro Asp Trp Gln Pro Tyr Leu Pro Gln Asn Gly Asp Asn
            530                 535                 540

Ile Glu Val Ala Phe Ser Tyr Ser Ser Val Leu Trp Pro Trp Ser Gly
545                 550                 555                 560

Tyr Leu Ala Ile Ser Ile Ser Val Thr Lys Lys Ala Ala Ser Trp Glu
                565                 570                 575

Gly Ile Ala Gln Gly His Val Met Ile Thr Val Ala Ser Pro Ala Glu
                580                 585                 590

Thr Glu Ser Lys Asn Gly Ala Glu Gln Thr Ser Thr Val Lys Leu Pro
            595                 600                 605

Ile Lys Val Lys Ile Ile Pro Thr Pro Pro Arg Ser Lys Arg Val Leu
            610                 615                 620

Trp Asp Gln Tyr His Asn Leu Arg Tyr Pro Pro Gly Tyr Phe Pro Arg
625                 630                 635                 640

Asp Asn Leu Arg Met Lys Asn Asp Pro Leu Asp Trp Asn Gly Asp His
                645                 650                 655

Ile His Thr Asn Phe Arg Asp Met Tyr Gln His Leu Arg Ser Met Gly
                660                 665                 670

Tyr Phe Val Glu Val Leu Gly Ala Pro Phe Thr Cys Phe Asp Ala Ser
                675                 680                 685

Gln Tyr Gly Thr Leu Leu Met Val Asp Ser Glu Glu Glu Tyr Phe Pro
            690                 695                 700

Glu Glu Ile Ala Lys Leu Arg Arg Asp Val Asp Asn Gly Leu Ser Leu
705                 710                 715                 720

Val Ile Phe Ser Asp Trp Tyr Asn Thr Ser Val Met Arg Lys Val Lys
                725                 730                 735

Phe Tyr Asp Glu Asn Thr Arg Gln Trp Trp Met Pro Asp Thr Gly Gly
                740                 745                 750

Ala Asn Ile Pro Ala Leu Asn Glu Leu Leu Ser Val Trp Asn Met Gly
                755                 760                 765

Phe Ser Asp Gly Leu Tyr Glu Gly Glu Phe Thr Leu Ala Asn His Asp
770                 775                 780

Met Tyr Tyr Ala Ser Gly Cys Ser Ile Ala Lys Phe Pro Glu Asp Gly
785                 790                 795                 800

Val Val Ile Thr Gln Thr Phe Lys Asp Gln Gly Leu Glu Val Leu Lys
                805                 810                 815

Gln Glu Thr Ala Val Val Glu Asn Val Pro Ile Leu Gly Leu Tyr Gln
                820                 825                 830

Ile Pro Ala Glu Gly Gly Arg Ile Val Leu Tyr Gly Asp Ser Asn
                835                 840                 845

Cys Leu Asp Asp Ser His Arg Gln Lys Asp Cys Phe Trp Leu Leu Asp
                850                 855                 860

Ala Leu Leu Gln Tyr Thr Ser Tyr Gly Val Thr Pro Pro Ser Leu Ser
865                 870                 875                 880

His Ser Gly Asn Arg Gln Arg Pro Pro Ser Gly Ala Gly Ser Val Thr
                885                 890                 895

Pro Glu Arg Met Glu Gly Asn His Leu His Arg Tyr Ser Lys Val Leu
            900                 905                 910
```

-continued

```
Glu Ala His Leu Gly Asp Pro Lys Pro Arg Pro Leu Pro Ala Cys Pro
        915             920             925

Arg Leu Ser Trp Ala Lys Pro Gln Pro Leu Asn Glu Thr Ala Pro Ser
        930             935             940

Asn Leu Trp Lys His Gln Lys Leu Leu Ser Ile Asp Leu Asp Lys Val
945             950             955             960

Val Leu Pro Asn Phe Arg Ser Asn Arg Pro Gln Val Arg Pro Leu Ser
            965             970             975

Pro Gly Glu Ser Gly Ala Trp Asp Ile Pro Gly Gly Ile Met Pro Gly
            980             985             990

Arg Tyr Asn Gln Glu Val Gly Gln Thr Ile Pro Val Phe Ala Phe Leu
        995             1000            1005

Gly Ala Met Val Val Leu Ala Phe Phe Val Val Gln Ile Asn Lys Ala
    1010            1015            1020

Lys Ser Arg Pro Lys Arg Arg Lys Pro Arg Val Lys Arg Pro Gln Leu
1025            1030            1035            1040

Met Gln Gln Val His Pro Pro Lys Thr Pro Ser Val
                1045            1050
```